(12) United States Patent
Tomoda et al.

(10) Patent No.: US 11,407,742 B2
(45) Date of Patent: Aug. 9, 2022

(54) COMPOUND HAVING THERAPEUTIC ACTIVITY AGAINST MYCOBACTERIUM AVIUM COMPLEX INFECTION, AND METHOD FOR PRODUCING SAME

(71) Applicants: THE KITASATO INSTITUTE, Tokyo (JP); OP BIO FACTORY CO., LTD., Uruma (JP)

(72) Inventors: Hiroshi Tomoda, Kanagawa (JP); Nobuhiro Koyama, Kanagawa (JP); Akihiko Kanamoto, Okinawa (JP); Junko Hashimoto, Tokyo (JP); Ikuko Kozone, Tokyo (JP)

(73) Assignees: THE KITASATO INSTITUTE, Tokyo (JP); OP BIO FACTORY CO., LTD., Okinawa (JP)

( * ) Notice: Subject to any disclaimer, the term of this patent is extended or adjusted under 35 U.S.C. 154(b) by 114 days.

(21) Appl. No.: 16/643,347

(22) PCT Filed: Aug. 30, 2018

(86) PCT No.: PCT/JP2018/032048
§ 371 (c)(1),
(2) Date: Feb. 28, 2020

(87) PCT Pub. No.: WO2019/044941
PCT Pub. Date: Mar. 7, 2019

(65) Prior Publication Data
US 2020/0407346 A1 Dec. 31, 2020

(30) Foreign Application Priority Data

Sep. 1, 2017 (JP) .............................. JP2017-168404

(51) Int. Cl.
C07D 405/14 (2006.01)
A61P 31/04 (2006.01)
C07H 17/04 (2006.01)

(52) U.S. Cl.
CPC ........... *C07D 405/14* (2013.01); *A61P 31/04* (2018.01); *C07H 17/04* (2013.01)

(58) Field of Classification Search
None
See application file for complete search history.

(56) References Cited

U.S. PATENT DOCUMENTS 2,909,517 A 10/1959 De Boer et al.
3,308,117 A 3/1967 Kelly et al.
3,309,273 A 3/1967 Bergy et al.

FOREIGN PATENT DOCUMENTS

JP 2010-535797 A 11/2010
WO WO 2009/023473 A2 2/2009
WO WO 2013/144894 A1 10/2013

OTHER PUBLICATIONS

International Search Report dated Nov. 27, 2018, in PCT/JP2018/032048.
Bu et al., "Anti-Mycobacterial Nucleoside Antibiotics from a Marine-Derived *Streptomyces* sp. TPU1236A," Marine Drugs, 2014, 12:6102-6112.
Lichtenthaler et al., "Structural Basis for Inhibition of Protein Synthesis by the Aminoacyl-Aminohexosyl-Cytosine Group of Antibiotics," FEBS Letters, Jan. 1974, 38(3):237-242.
Tatsuoka et al,. "Studies on Antibiotics, V: Extraction and Physicochemical Properties of Allomycin, an Antituberculous Antibiotic, and its Identity with Amicetin," Yakugaku Zasshi, 1955, 75:1206-1208.
Tatsuoka et al., "Studies on Antibiotics, VII: Antagonistic Properties of Amicetin with Antifungal-Antiprotozoal Antibiotics in vitro," Yakugaku Zasshi, 1955, 75:1276-1281.
Haskell, "Amicetin, Bamicetin and Plicacetin. Chemical Studies," J. Am. Chem. Soc., Feb. 5, 1958, 80(3):747-751.
Shiomi et al., "Cytoaminomycins, New Anticoccidial Agents Produced by *Streptomyces* sp. KO-8119," The Journal of Antibiotics, Jul. 1994, 782-786.
Supplementary European Search Report dated Apr. 28, 2021 in EP 18849862.0.

*Primary Examiner* — Layla D Berry
(74) *Attorney, Agent, or Firm* — Foley & Lardner LLP

(57) ABSTRACT

The purpose of the present invention is to provide a novel compound which has antibacterial activity against *Mycobacterium avium* and *Mycobacterium intracellulare* that are causative bacteria of MAC infection and which is different in backbone structure from known drugs for treatment of MAC infection. One aspect of the present invention relates to a compound of Formula (I) [where $R^1$ has the same meaning as described in the specification and claims] or a salt thereof, or a solvate thereof. Another aspect of the present invention relates to a method for producing the compound of Formula (I) or a salt thereof, or a solvate thereof, and a therapeutic agent for *Mycobacterium avium* complex infection (MAC infection), which comprises the compound or a pharmaceutically acceptable salt thereof, or a pharmaceutically acceptable solvate thereof as an active ingredient.

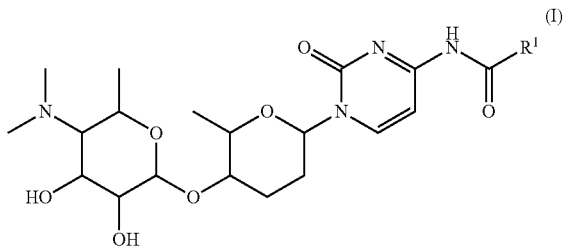

7 Claims, No Drawings

COMPOUND HAVING THERAPEUTIC ACTIVITY AGAINST MYCOBACTERIUM AVIUM COMPLEX INFECTION, AND METHOD FOR PRODUCING SAME

CROSS-REFERENCE TO RELATED APPLICATIONS

This application is the U.S. National Stage of PCT/JP2018/032048, filed Aug. 30, 2018, which claims priority to JP 2017-168404, filed Sep. 1, 2017.

TECHNICAL FIELD

The present invention relates to a novel compound having therapeutic activity against *Mycobacterium avium* complex infection (hereinafter, also referred to as "MAC infection"), and a method for producing the compound.

BACKGROUND ART

The MAC infection is a complex infection caused by *Mycobacterium avium* and *Mycobacterium intracellulare*. *Mycobacterium avium* and *Mycobacterium intracellulare* belong to nontuberculous mycobacteria which belong to acid-fast bacteria and are not tuberculosis bacteria. *Mycobacterium avium* and *Mycobacterium intracellulare* propagate to host animals from the surrounding environments such as soil, water and the like. It is known that in the bodies of host animals, these bacteria mainly infect the lung, which causes tuberculosis-like symptoms such as breathing difficulty.

The number of people developing infections caused by nontuberculous mycobacteria (hereinafter, also referred to as "nontuberculous mycobacteria infections") has increased worldwide, and among them, the number of people developing MAC infection has rapidly increased. In Japan, throughout 2014, the number of people who developed tuberculosis was 10.2 in relative to the population of 100,000, whereas the number of people who developed MAC infection was 14.7 in relative to the population of 100,000.

Currently, drugs for treatment of MAC infection are limited. Treatment using such drugs typically lasts for several years. A drug capable of completely curing MAC infection is not found at present. Therefore, development of a drug capable of treating MAC infection has been desired.

For example, Patent Literature 1 discloses a composition containing steffisburgensimycin. The literature suggests that steffisburgensimycin can inhibit growth of various gram-positive bacteria including *Mycobacterium avium*.

Patent Literature 2 discloses a method for treating an infection, including administering an effective amount of a formulation containing a compound having a specific structure to a patient in need of treatment of the infection through injection or transfusion, wherein the compound is dissolved in water together with an isotonic agent. In the literature, the infection is MAC infection.

CITATION LIST

Patent Literature

Patent Literature 1: U.S. Pat. No. 3,309,273
Patent Literature 2: JP Patent Publication (Kohyo) No. 2010-535797 A

SUMMARY OF INVENTION

Technical Problem

Drugs capable of treating MAC infection are known as taught in, for example, Patent Literatures 1 and 2. However, these literatures do not specifically show antibacterial activity against *Mycobacterium avium* and *Mycobacterium intracellulare* that are causative bacteria of MAC infection.

*Mycobacterium avium* and *Mycobacterium intracellulare* are classified as gram-positive bacteria. However, even a drug exhibiting antibacterial activity against gram-positive bacteria often fails to exhibit substantially high antibacterial activity against *Mycobacterium avium* and *Mycobacterium intracellulare*, when used alone. Thus, in treatment of MAC infection, a plurality of drugs are administered in combination over a long period of time. Such a dosage form may lay a significant burden on patients.

In bacterial infections, such as MAC infection, there may be a concern about emergence of drug-resistant bacteria. Therefore, in order to develop a more effective drug, a novel compound is desired, which has antibacterial activity against causative bacteria and which is different in backbone structure from known drugs.

Accordingly, an object of the present invention is to provide a novel compound which has antibacterial activity against *Mycobacterium avium* and *Mycobacterium intracellulare* that are causative bacteria of MAC infection and which is different in backbone structure from known drugs for treatment of MAC infection.

Solution to Problem

The present inventors have extensively conducted studies for solving the above-described problems. The present inventors have found that novel actinomycetes produce, in a culture broth thereof, a compound having antibacterial activity against *Mycobacterium avium* and *Mycobacterium intracellulare*. The present inventors have found that the compound in the culture broth is a novel compound different in backbone structure from known drugs for treatment of MAC infection. The present inventors have found that the compound can be produced by culturing means with such bacteria. The present inventors have completed the present invention on the basis of the above-described findings.

Specifically, the subject matters of the present invention are as follows.

(1) A compound of Formula (I):

[Formula 4]

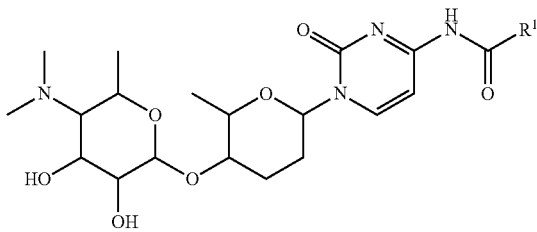

(I)

wherein, $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, substituted or unsubstituted acyloxy, substituted or unsubstituted biphenyl, substituted or unsubstituted terphenyl, substituted or unsubstituted naphthyl, substituted or unsubstituted anthracenyl, or

[Formula 2]

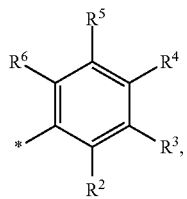

wherein,

* represents a binding position with a remainder, $R^2$, $R^3$, $R^5$ and $R^6$ are each independently hydrogen, halogen (fluorine, chlorine, bromine or iodine), cyano, nitro, hydroxyl, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted aryl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted heteroaryloxy, substituted or unsubstituted heteroarylalkyloxy, substituted or unsubstituted alkoxycarbonyl, substituted or unsubstituted cycloalkoxycarbonyl, substituted or unsubstituted acyl, substituted or unsubstituted acyloxy, or substituted or unsubstituted amino, and $R^4$ is hydrogen, halogen (fluorine, chlorine, bromine or iodine), cyano, hydroxyl, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted aryl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted heteroaryloxy, substituted or unsubstituted heteroarylalkyloxy, substituted or unsubstituted alkoxycarbonyl, substituted or unsubstituted cycloalkoxycarbonyl, substituted or unsubstituted acyl, substituted or unsubstituted acyloxy, 2-methylpropionylamino, or 4-hydroxymethyl-2,2,4-trimethyl-5-oxoimidazolizin-1-yl, or a salt thereof, or a solvate thereof.

(2) The compound according to embodiment (1), wherein $R^1$ is substituted or unsubstituted $C_1$-$C_6$ alkyl, substituted or unsubstituted $C_2$-$C_6$ alkenyl, substituted or unsubstituted $C_2$-$C_6$ alkynyl, or

[Formula 3]

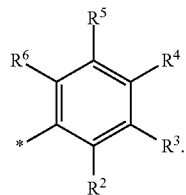

(3) The compound according to embodiment (1), wherein $R^1$ is 2-methylpropan-1-en-yl.

(4) A method for producing the compound or a salt thereof, or a solvate thereof according to any one of embodiments (1) to (3), which comprises:

a compound accumulation step of culturing in a medium a microorganism which is *Streptomyces* OPMA40551 strain (Accession No. NITE BP-02510) or a variant thereof capable of producing the compound of Formula (I) to accumulate the compound of Formula (I) in the medium; and a compound purification step of purifying, from a culture broth of the microorganism, the compound of Formula (I) obtained in the compound accumulation step.

(5) A microorganism which is *Streptomyces* OPMA40551 strain (Accession No. NITE BP-02510) or a variant thereof capable of producing the compound of Formula (I) according to any one of embodiments (1) to (3).

(6) A therapeutic agent for *Mycobacterium avium* complex infection (MAC infection), comprising the compound or a pharmaceutically acceptable salt thereof, or a pharmaceutically acceptable solvate thereof according to any one of embodiments (1) to (3) as an active ingredient.

(7) A medicament comprising the compound or a pharmaceutically acceptable salt thereof, or a pharmaceutically acceptable solvate thereof according to any one of embodiments (1) to (3) as an active ingredient.

(8) The medicament according to embodiment (7) for use in preventing or treating *Mycobacterium avium* complex infection (MAC infection).

(9) A pharmaceutical composition comprising the compound or a pharmaceutically acceptable salt thereof, or a pharmaceutically acceptable solvate thereof according to any one of embodiments (1) to (3), and one or more pharmaceutically acceptable carriers.

(10) The pharmaceutical composition according to embodiment (9) for use in preventing or treating *Mycobacterium avium* complex infection (MAC infection).

(11) A method for preventing or treating a symptom, disease and/or disorder which is an infection with one or more bacteria, which comprises administering an effective amount of the compound or a pharmaceutically acceptable salt thereof, or a pharmaceutically acceptable solvate thereof according to any one of embodiments (1) to (3) to a subject in need of prevention or treatment of the symptom, disease and/or disorder.

(12) The method according to embodiment (11), wherein the symptom, disease and/or disorder which is an infection with one or more bacteria is one or more symptoms, diseases and/or disorders selected from the group consisting of *Mycobacterium avium* complex infection (MAC infection) and tuberculosis.

(13) The compound or a pharmaceutically acceptable salt thereof, or a pharmaceutically acceptable solvate thereof according to any one of embodiments (1) to (3) for use in preventing or treating a symptom, disease and/or disorder which is an infection with one or more bacteria.

(14) The compound according to embodiment (13), wherein the symptom, disease and/or disorder which is an infection with one or more bacteria is one or more symptoms, diseases and/or disorders selected from the group consisting of *Mycobacterium avium* complex infection (MAC infection) and tuberculosis.

(15) Use of the compound or a pharmaceutically acceptable salt thereof, or a pharmaceutically acceptable solvate thereof according to any one of embodiments (1) to (3) in the manufacture of a medicament for preventing or treating a symptom, disease and/or disorder which is an infection with one or more bacteria.

(16) The use according to embodiment (15), wherein the symptom, disease and/or disorder which is an infection with one or more bacteria is one or more symptoms, diseases and/or disorders selected from the group consisting of *Mycobacterium avium* complex infection (MAC infection) and tuberculosis.

Advantageous Effects of Invention

According to the present invention, it is possible to provide a novel compound which has antibacterial activity against *Mycobacterium avium* and *Mycobacterium intracellulare* that are causative bacteria of MAC infection and which is different in backbone structure from known drugs for treatment of MAC infection.

Objects, configurations and effects other than those described above will be made evident by referring to the following embodiments.

The present specification incorporates the contents described in the specification and/or the drawings of JP Patent Application No. 2017-168404 based on which priority to the present application is claimed.

DESCRIPTION OF EMBODIMENTS

Hereinafter, preferred embodiments of the present invention will be described in detail.
<1. Novel Compound>
In the present specification, the "alkyl" means a linear or branched saturated aliphatic hydrocarbon group containing a specific number of carbon atoms. For example, the "$C_1$-$C_5$ alkyl" means a linear or branched saturated aliphatic hydrocarbon group containing at least 1 and at most 5 carbon atoms, and the "$C_1$-$C_6$ alkyl" means a linear or branched saturated aliphatic hydrocarbon group containing at least 1 and at most 6 carbon atoms. Examples of preferred alkyl include, but are not limited to, linear or branched $C_1$-$C_5$ alkyl such as methyl, ethyl, n-propyl, isopropyl, n-butyl, sec-butyl, isobutyl, tert-butyl and n-pentyl, and linear or branched $C_1$-$C_6$ alkyl such as n-hexyl and methylpentyl.

In the present specification, the "alkenyl" means a group in which one or more C—C single bonds of the alkyl are replaced by double bonds. Examples of preferred alkenyl include, but are not limited to, linear or branched $C_2$-$C_5$ alkenyls such as vinyl, 1-propenyl, allyl, 1-methylethenyl (isopropenyl), 1-butenyl, 2-butenyl, 3-butenyl, 1-methyl-2-propenyl, 2-methyl-2-propenyl, 1-methyl-1-propenyl, 2-methyl-1-propenyl and 1-pentenyl, and linear or branched $C_1$-$C_6$ alkenyls such as 1-hexenyl and methylpentenyl.

In the present specification, the "alkynyl" means a group in which one or more C—C single bonds of the alkyl are replaced by triple bonds. Examples of preferred alkynyl include, but are not limited to, linear or branched $C_2$-$C_5$ alkynyls such as ethynyl, 1-propynyl, 2-propynyl, 1-butynyl, 2-butynyl, 3-butynyl, 1-methyl-2-propynyl and 1-pentynyl, and linear or branched $C_1$-$C_6$ alkynyls such as 1-hexynyl and methylpentynyl.

In the present specification, the "cycloalkyl" means a cycloaliphatic alkyl containing a specific number of carbon atoms. For example, the "$C_3$-$C_6$ cycloalkyl" means a cyclic hydrocarbon group containing at least 3 and at most 6 carbon atoms. Examples of preferred cycloalkyl include, but are not limited to, $C_3$-$C_6$ cycloalkyl such as cyclopropyl, cyclobutyl, cyclopentyl and cyclohexyl.

In the present specification, the "cycloalkenyl" means a group in which one or more C—C single bonds of the cycloalkyl are replaced by double bonds. Examples of preferred cycloalkenyl include, but are not limited to, $C_4$-$C_6$ cycloalkenyls such as cyclobutenyl, cyclopentenyl and cyclohexenyl.

In the present specification, the "cycloalkynyl" means a group in which one or more C—C single bonds of the cycloalkyl are replaced by triple bonds. Examples of preferred cycloalkynyl include, but are not limited to, $C_4$-$C_6$ cycloalkynyls such as cyclobutynyl, cyclopentynyl and cyclohexynyl.

In the present specification, the "heterocycloalkyl" means a group in which one or more carbon atoms of the cycloalkyl, cycloalkenyl or cycloalkynyl are each independently replaced by one or more heteroatoms selected from nitrogen, sulfur and oxygen. In this case, the replacement by N or S includes replacement by N-oxides or oxides or dioxides of S. Examples of preferred heterocycloalkyl include, but are not limited to, three- to six-membered heterocycloalkyl such as pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl and piperazinyl.

In the present specification, the "cycloalkylalkyl" means a group in which one of hydrogen atoms of the alkyl, alkenyl or alkynyl is replaced by the cycloalkyl, cycloalkenyl or cycloalkynyl. Examples of preferred cycloalkylalkyl include, but are not limited to, $C_7$-$C_{11}$ cycloalkylalkyl such as cyclohexylmethyl and cyclohexenylmethyl.

In the present specification, the "heterocycloalkylalkyl" means a group in which one of hydrogen atoms of the alkyl, alkenyl or alkynyl is replaced by the heterocycloalkyl. Examples of preferred heterocycloalkylalkyl include, but are not limited to, three- to six-membered heterocycloalkyl-$C_1$-$C_5$ alkyl.

In the present specification, the "alkoxy" means a group in which the hydrogen atom of hydroxyl is replaced by the alkyl, alkenyl or alkynyl. Examples of preferred alkoxy include, but are not limited to, $C_1$-$C_5$ alkoxy such as methoxy, ethoxy, propoxy, butoxy and pentoxy.

In the present specification, the "cycloalkoxy" means a group in which the hydrogen atom of hydroxyl is replaced by the cycloalkyl, cycloalkenyl or cycloalkynyl. Examples of preferred cycloalkoxy include, but are not limited to, $C_3$-$C_6$ cycloalkoxy such as cyclopropoxy, cyclobutoxy and cyclopentoxy.

In the present specification, the "heterocycloalkoxy" means a group in which the hydrogen atom of hydroxyl is replaced by the heterocycloalkyl. Examples of preferred cycloalkoxy include, but are not limited to, three- to six-membered heterocycloalkoxy.

In the present specification, the "aryl" means an aromatic ring group. Examples of preferred aryl include, but are not limited to, $C_6$-$C_{18}$ aryls such as phenyl, biphenyl, terphenyl, naphthyl and anthracenyl.

In the present specification, the "arylalkyl" means a group in which one of hydrogen atoms of the alkyl, alkenyl or alkynyl is replaced by the aryl. Examples of preferred arylalkyl include, but are not limited to, $C_7$-$C_{20}$ arylalkyl such as benzyl, 1-phenethyl, 2-phenethyl, biphenylmethyl, terphenylmethyl and styryl.

In the present specification, the "heteroaryl" means a group in which one or more carbon atoms of the aryl are each independently replaced by one or more heteroatoms selected from N, S and O. In this case, the replacement by N or S includes replacement by N-oxides or oxides or dioxides of S. Examples of preferred heteroaryl include, but are not limited to, five- to fifteen-membered heteroaryls such as furanyl, thienyl (thiophenyl), pyrrolyl, imidazolyl, pyrazolyl, triazolyl, tetrazolyl, thiazolyl, oxazolyl, isoxazolyl, oxadiazolyl, thiadiazolyl, isothiazolyl, pyridyl, pyridazinyl, pyrazinyl, pyrimidinyl, quinolinyl, isoquinolinyl and indolyl.

In the present specification, the "heteroarylalkyl" means a group in which one of hydrogen atoms of the alkyl, alkenyl or alkynyl is replaced by the heteroaryl. Examples of preferred heteroarylalkyl include, but are not limited to, five- to fifteen-membered heteroaryl-$C_1$-$C_5$ alkyl such as pyridylmethyl.

In the present specification, the "aryloxy" means a group in which the hydrogen atom of hydroxyl is replaced by the aryl. Examples of preferred aryloxy include, but are not limited to, $C_6$-$C_{15}$ aryloxy such as phenoxy, biphenyloxy, naphthyloxy and anthryloxy (anthracenyloxy).

In the present specification, the "arylalkyloxy" means a group in which the hydrogen atom of hydroxyl is replaced by the arylalkyl. Examples of preferred arylalkyloxy include, but are not limited to, $C_7$-$C_{20}$ arylalkyloxy such as benzyloxy, 1-phenethyloxy, 2-phenethyloxy and styryloxy.

In the present specification, the "heteroaryloxy" means a group in which the hydrogen atom of hydroxyl is replaced by the heteroaryl. Examples of preferred heteroaryloxy include, but are not limited to, five- to fifteen-membered heteroaryloxy such as furanyloxy, thienyloxy (thiophenyloxy), pyrrolyloxy, imidazolyloxy, pyrazolyloxy, triazolyloxy, tetrazolyloxy, thiazolyloxy, oxazolyloxy, isoxazolyloxy, oxadiazolyloxy, thiadiazolyloxy, isothiazolyloxy, pyridyloxy, pyridazinyloxy, pyrazinyloxy, pyrimidinyloxy, quinolinyloxy, isoquinolinyloxy and indolyloxy.

In the present specification, the "heteroarylalkyloxy" means a group in which the hydrogen atom of hydroxyl is replaced by the heteroarylalkyl. Examples of preferred heteroarylalkyloxy include, but are not limited to, five- to fifteen-membered heteroaryl-$C_1$-$C_5$ alkyloxy.

In the present specification, the "acyl" means a group in which a monovalent group selected from the groups described above is linked to carbonyl. Examples of preferred acyl include, but are not limited to, $C_1$-$C_{20}$ acyl including $C_1$-$C_5$ aliphatic acyl such as formyl, acetyl and propionyl and $C_7$-$C_{120}$ aromatic acyl such as benzoyl.

The groups described above may be each independently unsubstituted, or substituted with one or more monovalent groups described above.

In the present specification, the "halogen" or "halo" means fluorine (F), chlorine (Cl), bromine (Br) or iodine (I).

One aspect of the present invention relates to a compound of Formula (I):

[Formula 4]

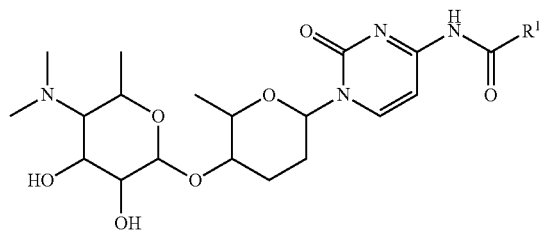

(I)

or a salt thereof, or a solvate thereof.

The present inventors have found that novel actinomycetes produce, in a culture broth thereof, a compound having antibacterial activity against *Mycobacterium avium* and *Mycobacterium intracellulare*. The present inventors have found novel compounds 40551-F, -D, -G, -H, -I, -K and -L having antibacterial activity against *Mycobacterium avium* and *Mycobacterium intracellulare* in the culture broth. These novel compounds, particularly compound 40551-F, have antibacterial activity, which is equivalent to or higher than that of conventional art antibacterial substances such as ethambutol, against *Mycobacterium avium* and *Mycobacterium intracellulare* which are causative bacteria of MAC infection. The present inventors have found that the compounds 40551-F, -D, -G, -H, -I, -K and -L have antibacterial activity against not only nontuberculous mycobacteria such as *Mycobacterium avium* and *Mycobacterium intracellulare* but also *Mycobacterium bovis* (*M. bovis*) having high genomic homology with *Mycobacterium tuberculosis* (*M. tuberculosis*). The compound (I) of Formula (I) in this aspect includes natural organic compounds 40551-F, D, -G, -H, -I, -K and -L, and similar compounds. Therefore, the compound of Formula (I) in this aspect can exhibit high antibacterial activity against nontuberculous mycobacteria such as *Mycobacterium avium* and *Mycobacterium intracellulare* which are causative bacteria of MAC infection. The compound of Formula (I) in this aspect can also exhibit antibacterial activity against tuberculosis bacteria such as *Mycobacterium tuberculosis* and *Mycobacterium bovis*.

In Formula (1), $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted aryalkenyloxy, substituted or unsubstituted heteroaryloxy, substituted or unsubstituted heteroarylalkyloxy, substituted or unsubstituted acyloxy, substituted or unsubstituted biphenyl, substituted or unsubstituted terphenyl, substituted or unsubstituted naphthyl, substituted or unsubstituted anthracenyl, or

[Formula 5]

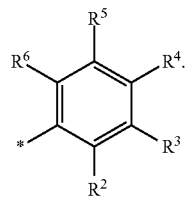

Here, * represents a binding position with a remainder. $R^1$ is preferably substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted $C_7$-$C_{20}$ arylalkenyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_{20}$ acyloxy, substituted or unsubstituted biphenyl, substituted or unsubstituted terphenyl, substituted or unsubstituted naphthyl, substituted or unsubstituted anthracenyl, or

[Formula 6]

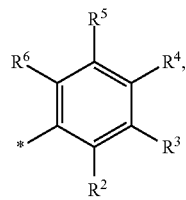

more preferably substituted or unsubstituted $C_1$-$C_6$ alkyl, substituted or unsubstituted $C_2$-$C_6$ alkenyl, substituted or unsubstituted $C_2$-$C_6$ alkynyl, or

[Formula 7]

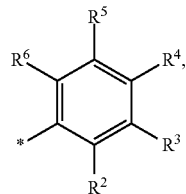

still more preferably substituted or unsubstituted $C_1$-$C_6$ alkyl, substituted or unsubstituted $C_2$-$C_6$ alkenyl, substituted or unsubstituted $C_2$-$C_6$ alkynyl, 4-(2-methylpropionylamino)-phenyl, or 4-(4-hydroxymethyl-2,2,4-trimethyl-5-oxoimidazolidin-1-yl)-phenyl, furthermore preferably 2-methylpropan-1-en-yl, 4-(2-methylpropionylamino)-phenyl, 3-methylpentan-1-en-yl, 4-(4-hydroxymethyl-2,2,4-trimethyl-5 oxoimidazolidin-1-yl)-phenyl, 1-methylpropan-1-en-yl, 1-methylpropyl or 3-methylbutan-1-en-yl, particularly preferably 2-methylpropan-1-en-yl. When $R^1$ is a group exemplified above, the compound of Formula (I) in this aspect can exhibit particularly high antibacterial activity against nontuberculous mycobacteria such as *Mycobacterium avium* and *Mycobacterium intracellulare* which are causative bacteria of MAC infection. In this case, the compound of Formula (I) in this aspect can also exhibit high antibacterial activity against tuberculosis bacteria.

In Formula (I), $R^2$, $R^3$, $R^5$ and $R^6$ are each independently hydrogen, halogen (fluorine, chlorine, bromine or iodine), cyano, nitro, hydroxyl, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted aryl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted heteroaryloxy, substituted or unsubstituted heteroarylalkyloxy, substituted or unsubstituted alkoxycarbonyl, substituted or unsubstituted cycloalkoxycarbonyl, substituted or unsubstituted acyl, substituted or unsubstituted acyloxy, or substituted or unsubstituted amino. $R^2$, $R^3$, $R^5$ and $R^6$ are preferably each independently hydrogen, halogen (fluorine, chlorine, bromine or iodine), cyano, nitro, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_5$ alkoxycarbonyl, substituted or unsubstituted $C_3$-$C_6$ cycloalkoxycarbonyl, substituted or unsubstituted $C_1$-$C_5$ acyl, substituted or unsubstituted $C_1$-$C_5$ acyloxy, or substituted or unsubstituted amino, more preferably each independently hydrogen, halogen (fluorine, chlorine, bromine or iodine), hydroxyl, or substituted or unsubstituted amino, and still more preferably they all are hydrogen.

In Formula (I), $R^4$ is hydrogen, halogen (fluorine, chlorine, bromine or iodine), cyano, hydroxyl, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted aryl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted heteroaryloxy, substituted or unsubstituted heteroarylalkyloxy, substituted or unsubstituted alkoxycarbonyl, substituted or unsubstituted cycloalkoxycarbonyl, substituted or unsubstituted acyl, substituted or unsubstituted acyloxy, 2-methylpropionylamino, or 4-hydroxymethyl-2,2,4-trimethyl-5-oxoimidazolizin-1-yl. $R^4$ is preferably hydrogen, halogen (fluorine, chlorine, bromine or iodine), cyano, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_5$ alkoxycarbonyl, substituted or unsubstituted $C_3$-$C_6$ cycloalkoxycarbonyl, substituted or unsubstituted $C_1$-$C_5$ acyl, substituted or unsubstituted $C_1$-$C_5$ acyloxy, 2-methylpropionylamino, or 4-hydroxymethyl-2,2,4-trimethyl-5-oxoimidazolidin-1-yl, more preferably hydrogen, halogen (fluorine, chlorine, bromine or iodine), hydroxyl, 2-methylpropionylamino, or 4-hydroxymethyl-2,2,4-trimethyl-5-oxoimidazolidin-1-yl, still more preferably hydrogen.

When the above-described groups are substituted in Formula (I), the substituents are preferably each independently at least one monovalent group selected from the group consisting of halogen (fluorine, chlorine, bromine or iodine), cyano, nitro, hydroxyl, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted cycloalkylalkyl, substituted or unsubstituted heterocycloalkylalkyl, substituted or unsubstituted aryl, substituted or unsubstituted arylalkyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted heteroaryloxy, substituted or unsubstituted heteroarylalkyloxy, substituted or unsubstituted alkoxycarbonyl, substituted or unsubstituted cycloalkoxycarbonyl, substituted or unsubstituted acyl, substituted or unsubstituted acyloxy and substituted or unsubstituted amino, more preferably each independently at least one monovalent group selected from the group consisting of halogen (fluorine, chlorine, bromine or iodine), cyano, nitro, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_6$ alkoxycarbonyl, substituted or unsubstituted $C_3$-$C_6$ cycloalkoxycarbonyl, substituted or unsubstituted $C_1$-$C_{20}$ acyl, substituted or unsubstituted $C_1$-$C_{20}$ acyloxy, or substituted or unsubstituted amino, still more preferably at least one monovalent group selected from the group consisting of hydroxyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy and substituted or unsubstituted $C_1$-$C_{20}$ acyloxy, particularly preferably hydroxyl. When the above-described monovalent groups are substituted, the substituents are each selected preferably further from the monovalent groups, more preferably further from the unsubstituted monovalent groups.

The compound of Formula (I) may include compounds defined by any combination of $R^1$, $R^2$, $R^3$, $R^4$, $R^5$ and $R^6$ exemplified above.

Preferably, the compound of Formula (I) is a compound in which $R^1$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted $C_7$-$C_{20}$ arylalkenyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_{20}$ acyloxy, substituted or unsubstituted biphenyl, substituted or unsubstituted terphenyl, substituted or unsubstituted naphthyl, substituted or unsubstituted anthracenyl, or

[Formula 8]

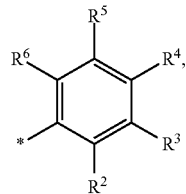

where $R^2$, $R^3$, $R^5$ and $R^6$ are each independently hydrogen, halogen (fluorine, chlorine, bromine or iodine), cyano, nitro, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, five- to fifteen-membered heteroaryl-$C_1$-$C_5$ alkyloxy, substituted or unsubstituted $C_1$-$C_5$ alkoxycarbonyl, substituted or unsubstituted $C_3$-$C_6$ cycloalkoxycarbonyl, substituted or unsubstituted $C_1$-$C_5$ acyl, substituted or unsubstituted $C_1$-$C_5$ acyloxy, or substituted or unsubstituted amino, $R^4$ is hydrogen, halogen (fluorine, chlorine, bromine or iodine), cyano, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_5$ alkoxycarbonyl, substituted or unsubstituted $C_3$-$C_6$ cycloalkoxycarbonyl, substituted or unsubstituted $C_1$-$C_5$ acyl, substituted or unsubstituted $C_1$-$C_5$ acyloxy, 2-methylpropionylamino, or 4-hydroxymethyl-2,2,4-trimethyl-5-oxoimidazolidin-1-yl, and when the above-described groups are substituted, the substituents are each independently at least one monovalent group selected from the group consisting of halogen (fluorine, chlorine, bromine or iodine), cyano, nitro, hydroxyl, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted three- to six-membered heterocycloalkyl, substituted or unsubstituted $C_7$-$C_{11}$ cycloalkylalkyl, substituted or unsubstituted three- to six-membered heterocycloalkyl-$C_1$-$C_5$ alkyl, substituted or unsubstituted $C_6$-$C_{15}$ aryl, substituted or unsubstituted $C_7$-$C_{20}$ arylalkyl, substituted or unsubstituted five- to fifteen-membered heteroaryl, substituted or unsubstituted five- to fifteen-membered heteroaryl-$C_1$-$C_5$ alkyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy, substituted or unsubstituted $C_1$-$C_5$ alkoxycarbonyl, substituted or unsubstituted $C_3$-$C_6$ cycloalkoxycarbonyl, substituted or unsubstituted $C_1$-$C_{20}$ acyl, substituted or unsubstituted $C_1$-$C_{20}$ acyloxy, substituted or unsubstituted amino. When the above-described monovalent groups are substituted, the substituents are each selected preferably further from the monovalent groups, more preferably further from the unsubstituted monovalent groups.

More preferably, the compound of Formula (I) is a compound in which $R^1$ is substituted or unsubstituted $C_1$-$C_6$ alkyl, substituted or unsubstituted $C_2$-$C_6$ alkenyl, substituted or unsubstituted $C_2$-$C_6$ alkynyl, or

[Formula 9]

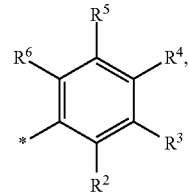

where $R^2$, $R^3$, $R^5$ and $R^6$ are each independently hydrogen, halogen (fluorine, chlorine, bromine or iodine), hydroxyl, or substituted or unsubstituted amino, $R^4$ is hydrogen, halogen (fluorine, chlorine, bromine or iodine), hydroxyl, 2-methylpropionylamino, or 4-hydroxymethyl-2,2,4-trimethyl-5-oxoimidazolidin-1-yl, and when the above-described groups are substituted, the substituents are each independently at least one monovalent group selected from the group consisting of hydroxyl, substituted or unsubstituted $C_1$-$C_6$ alkoxy, substituted or unsubstituted $C_3$-$C_6$ cycloalkoxy, substituted or unsubstituted three- to six-membered heterocycloalkoxy, substituted or unsubstituted $C_6$-$C_{15}$ aryloxy, substituted or unsubstituted $C_7$-$C_{20}$ arylalkyloxy, substituted or unsubstituted five- to fifteen-membered heteroaryloxy, substituted or unsubstituted five- to fifteen-membered heteroaryl-$C_1$-$C_5$ alkyloxy and substituted or unsubstituted $C_1$-$C_{20}$ acyloxy. When the above-described monovalent groups are substituted, the substituents are each selected preferably further from the monovalent groups, more preferably further from the unsubstituted monovalent groups.

Still more preferably, the compound of Formula (I) is a compound in which $R^1$ is substituted or unsubstituted $C_1$-$C_6$ alkyl, substituted or unsubstituted $C_2$-$C_6$ alkenyl, substituted or unsubstituted $C_2$-$C_6$ alkynyl, 4-(2-methylpropionylamino)-phenyl, or 4-(4-hydroxymethyl-2,2,4-trimethyl-5-oxoimidazolizin-1-yl)-phenyl, and when the above-described groups are substituted, the substituents are each independently at least one monovalent group selected from the group consisting of hydroxyl, unsubstituted $C_1$-$C_6$ alkoxy, unsubstituted $C_3$-$C_6$ cycloalkoxy, unsubstituted three- to six-membered heterocycloalkoxy, unsubstituted $C_6$-$C_{15}$ aryloxy, unsubstituted $C_7$-$C_{20}$ arylalkyloxy, unsubstituted five- to fifteen-membered heteroaryloxy, unsubstituted five- to fifteen-membered heteroaryl-$C_1$-$C_5$ alkyloxy and unsubstituted $C_1$-$C_{20}$ acyloxy. When the above-described monovalent groups are substituted, the substituents are each selected preferably further from the monovalent groups, more preferably further from the unsubstituted monovalent groups.

Furthermore preferably, the compound of Formula (I) is a compound in which $R^1$ is 2-methylpropan-1-en-yl, 4-(2-methylpropionylamino)-phenyl, 3-methylpentan-1-en-yl, 4-(4-hydroxymethyl-2,2,4-trimethyl-5-oxoimidazolidin-1-yl)-phenyl, 1-methylpropan-1-en-yl, 1-methylpropyl, or 3-methylbutan-1-en-yl.

Particularly preferably, the compound of Formula (I) is a compound in which $R^1$ is 2-methylpropan-1-en-yl.

Particularly preferable compounds of Formula (I) are the following compounds:

N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-3-methylbuta-2-enamide (40551-F);

N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)isobutyramide (40551-D);

(E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl-4-methylhex-2-enamide (40551-G);

1-(5-((5-(dimethylamino)-3,4-dihydroxy-6-methyltetrahydro-2H-pyran-2-yl)oxy)-6-methyltetrahydro-2H-pyran-2-yl)-4-(4-(hydroxymethyl)-2,2,4-trimethyl-5-oxoimidazolidin-1-yl)pyrimidine-2(1H)-one (40551-H);

(E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-2-methylbuta-2-enamide (40551-1);

N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-3-butanamide (40551-K); and (E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-4-methylpenta-2-enamide (40551-L).

An especially preferable compound of Formula (I) is the following compound:

N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-3-methylbuta-2-enamide (40551-F). When the compound of Formula (I) in this aspect is the above-described compound, the compound can exhibit particularly high antibacterial activity against nontuberculous mycobacteria such as *Mycobacterium avium* and *Mycobacterium intracellulare* which are causative bacteria of MAC infection. In this case, the compound of Formula (I) in this aspect can also exhibit antibacterial activity against tuberculosis bacteria.

The compound of Formula (I) in one aspect of the present invention includes not only the compound itself, but also salts thereof. Examples of preferred salts of the compound of Formula (I) in one aspect of the present invention include, but are not limited to, salts with a cation such as sodium ion, potassium ion, calcium ion, magnesium ion or substituted or unsubstituted ammonium ion, or an anion of inorganic acids such as hydrochloric acid, hydrobromic acid, sulfuric acid, nitric acid, carbonic acid and phosphoric acid, and organic acids such as formic acid, acetic acid, maleic acid, fumaric acid, benzoic acid, ascorbic acid, succinic acid, bismethylenesalicylic acid, methanesulfonic acid, ethanedisulfonic acid, propionic acid, tartaric acid, salicylic acid, citric acid, gluconic acid, aspartic acid, stearic acid, palmitic acid, itaconic acid, glycolic acid, p-aminobenzoic acid, glutamic acid, benzenesulfonic acid, cyclohexylsulfamic acid, methanesulfonic acid, ethanesulfonic acid, isethionic acid, p-toluenesulfonic acid and naphthalenesulfonic acid. Even when the compound of Formula (I) is in the form of the above-described salt, it is possible to exhibit high antibacterial activity against nontuberculous mycobacteria such as *Mycobacterium avium* and *Mycobacterium intracellulare* which are causative bacteria of MAC infection. In this case, the compound of Formula (I) in one aspect of the present invention can also exhibit antibacterial activity against tuberculosis bacteria.

The compound of Formula (I) in one aspect of the present invention includes not only the compound itself, but also solvates of the compound or salts thereof. Examples of solvents which can form solvates with the compound or a salt thereof include, but are not limited to, water, and organic solvents such as lower alcohols (e.g. alcohols having 1 to 6 carbon atoms, such as methanol, ethanol or 2-propanol (isopropyl alcohol)), higher alcohols (e.g. alcohols having 7 or more carbon atoms, such as 1-heptanol or 1-octanol), dimethyl sulfoxide (DMSO), acetic acid, ethanolamine and ethyl acetate. Even when the compound of Formula (I) or a salt thereof is in the form of the solvate with the above-described solvent, it is possible to exhibit high antibacterial activity against nontuberculous mycobacteria such as *Mycobacterium avium* and *Mycobacterium intracellulare* which are causative bacteria of MAC infection. In this case, the compound of Formula (I) in one aspect of the present invention can also exhibit antibacterial activity against tuberculosis bacteria.

The compound of Formula (I) in one aspect of the present invention includes not only the compound itself, but also protective structures thereof. In the present specification, the "protective form" means a form in which protective groups are introduced to one or more functional groups (e.g. an amino group, a hydroxyl group or a carboxylic acid group). In the present specification, the protective form of the compound represented by each formula described above is sometimes referred to as a protective derivative of the compound represented by each formula described above. In the present specification, the "protective group" means a group which is introduced to a specific functional group for preventing progress of undesired reaction and which is quantitatively removed under specific reaction conditions, and is substantially stable, that is, inert to reaction, under other reaction conditions. Examples of preferred protective groups which can form a protective form of the compound include, but are not limited to, t-butoxycarbonyl (Boc), 2-bromobenzyloxycarbonyl (BrZ) and 9-fluorenylmethoxycarbonyl (Fmoc) for protective groups for an amino group; silyl (e.g. t-butyldimethylsilyl (TBS), triisopropylsilyl (TIPS) and tert-butyldiphenylsilyl (TBDPS)) and alkoxy (e.g. methoxymethoxy (MOM) and methoxy (Me)) for protective groups for a hydroxyl group; and alkyl esters (e.g. methyl, ethyl and isopropyl esters), arylalkyl esters (e.g. benzyl esters) and amides (e.g. amides with oxazolidinones) for protective groups for carboxylic acid groups. A person skilled in the art can appropriately perform protection with the protective group and deprotection of it on the basis of known reaction conditions. Even when the compound of Formula (I) in one aspect of the present invention is a protective form with the above-described protective group, it may be possible to exhibit antibacterial activity against nontuberculous mycobacteria which are causative bacterial of MAC infection, such as *Mycobacterium avium* and *Mycobacterium intracellulare*, or against tuberculosis bacteria.

When the compound of Formula (I) in one aspect of the present invention has one or more tautomers, the compound includes a form of individual tautomers of the compound.

When the compound of Formula (I) in one aspect of the present invention has one or more stereocenters (chiral centers), the compound includes individual enantiomers and diastereomers of the compound, and mixtures thereof such as racemates.

Owing to the above-described characteristics, the compound of Formula (I) in one aspect of the present invention can exhibit high antibacterial activity against nontuberculous mycobacteria such as *Mycobacterium avium* and *Mycobacterium intracellulare* which are causative bacteria of MAC infection. The compound of Formula (I) in one aspect of the present invention can also exhibit antibacterial activity against tuberculosis bacteria.

<2. Method for Producing Novel Compound by Culturing Means>

The present inventors have found that novel actinomycetes produce compounds 40551-F, -D, -G, -H, -I, -K and -L, which are included in the compound of Formula (I) in one aspect of the present invention, in a culture broth of the actinomycetes. Thus, another aspect of the present invention relates to a method for producing the compound of Formula (I) in one aspect of the present invention with the use of novel actinomycetes.

In this aspect, the method of the present invention includes a compound accumulation step and a compound purification step. Hereinafter, the steps will be described in detail.

[2-1. Compound Accumulation Step]

In this aspect, the method of the present invention includes a compound accumulation step of culturing in a medium a microorganism which is *Streptomyces* OPMA40551 strain (Accession No. NITE BP-02510) or a variant thereof capable of producing the compound of Formula (I) to accumulatie the compound of Formula (I) in the medium.

The *Streptomyces* OPMA40551 strain is a novel actinomycete belonging to *Streptomyces* and separated in Japan. The strain was internationally deposited as OPMA40551 (Accession No. NITE BP-02510) under the Budapest Treaty on Jul. 18, 2017 at National Institute of Technology and Evaluation, Patent Microorganisms Depository Center (#122, 2-5-8, Kazusakamatari, Kisarazu-shi, Chiba, 292-0818 Japan).

In this step, the microorganism to be used for culture is preferably *Streptomyces* OPMA40551 strain or a variant thereof capable of producing the compound of Formula (I), more preferably *Streptomyces* OPMA40551 strain. In the present invention, the variant of *Streptomyces* OPMA40551 strain means a natural variant or an artificial variant thereof. The artificial variant of *Streptomyces* OPMA40551 strain can be obtained by any artificial variant production means which is commonly used in the art. In this step, the compound of Formula (I) can be accumulated in the medium not only with *Streptomyces* OPMA40551 strain itself, but also a variant of *Streptomyces* OPMA40551 strain as long as the variant is a microorganism capable of producing the compound of Formula (I). Thus, use of the microorganism enables a large amount of the compound of Formula (I) to be accumulated in the medium.

The medium to be used for culture of a microorganism can be appropriately selected according to the properties of the microorganism. The medium typically contains one or more carbon sources and one or more nitrogen sources, and optionally one or more inorganic salts and one or more vitamins. Examples of the carbon sources include saccharides such as glucose, fructose, maltose, lactose, galactose, dextrin and starch, and vegetable oils such as soybean oil. Examples of the nitrogen sources include polypeptone, yeast extract, malt extract, meat extract, soybean flour, cottonseed powder, corn steep liquor, casein, amino acids, urea, ammonium salts and nitric acid salts. Examples of the inorganic salts include salts between cations such as sodium ion, potassium ion, calcium ion, magnesium ion, iron ion, manganese ion, copper ion, cobalt ion and zinc ion, and anions of inorganic acids such as hydrochloric acid, sulfuric acid, nitric acid, carbonic acid and phosphoric acid. Examples of the medium used in this step include sea water-prepared ISP2 agar medium (yeast extract: 0.20% (DIFCO), malt extract: 0.50% (DIFCO), glucose: 0.20% (Wako Pure Chemical Industries, Ltd.), Artificial Sea Water Marine Art SF-1: 1.92% (Tomita Pharmaceutical Co., Ltd.), tap water: 1.0 L, natural sea water: 1.0 L (Deep Ocean), agar: 1.0% (SSK Sales Co. Ltd.), pH: adjusted to 7.3), and SPY medium (soluble starch: 1.0% (Wako Pure Chemical Industries, Ltd.), peptone: 0.50% (DIFCO), yeast extract: 0.25% (DIFCO), natural sea water (Deep Ocean), pH: not adjusted). The compound of Formula (I) can be accumulated in the medium by culturing in the medium a microorganism which is *Streptomyces* OPMA40551 strain capable of producing the compound of Formula (I), or a variant thereof.

The culture of the microorganism may be solid culture or liquid culture. When the microorganism is cultured on a large scale, liquid culture is preferable. In this case, it is preferable to aerate the medium by shaking of a culture vessel or stirring of the medium with a propeller or the like, or blowing air with a pump or the like. Preferably, the air to be introduced into the medium is sterilized with sterilization means such as a sterilizing filter. The compound of Formula (I) can be efficiently accumulated in the medium by culturing the microorganism under the above-described conditions.

When the microorganism is cultured on a large scale, it is preferable to culture the microorganism in a small amount of a medium in advance (hereinafter, also referred to as "seed culture"), followed by inoculating and culturing the cultured product obtained by the seed culture in a large volume of a medium (hereinafter, also referred to as "production culture"). In this case, the media used in the seed culture and the production culture may have the same or different components. Delay of growth of the microorganism can be substantially suppressed by carrying out this step in multi-stage culture including seed culture and production culture.

In this step, conditions for culturing the microorganism can be set according to the properties of the microorganism. The culture temperature is normally in the range of 15 to 37° C., typically about 25° C. The pH of the medium is normally 6 to 8, typically 7.3. When shaking culture is performed with a liquid medium, the culture period is normally 3 to 12 days, typically 5 to 10 days in terms of a total period of seed culture and production culture. The compound of Formula (I) can be efficiently accumulated in the medium by culturing the microorganism under the above-described conditions.

[2-2. Compound Accumulation Step]

In this aspect, the method of the present invention is required to include a compound purification step of purifying, from a culture of the microorganism, the compound of Formula (I) obtained in the compound accumulation step.

As means for purifying the compound of Formula (I) from the culture of the microorganism in this step, methods for separating an organic compound which are commonly used in the art can be used. Examples of the means for purifying the compound of Formula (I) from the culture of the microorganism include extraction, filtration, centrifugation, adsorption, recrystallization, distillation and various kinds of chromatography. Preferably, this step includes the steps of: separating mycelia from the culture of the microorganism obtained in the compound accumulation step by filtration, centrifugation or the like; extracting the separated mycelia with an organic solvent such as ethyl acetate; and further separating the mycelium extract extracted with the organic solvent by means such as solvent extraction or preparative chromatography to obtain the compound of Formula (I). As the preparative chromatography, various kinds of chromatography such as adsorption chromatography, normal phase or reversed phase chromatography or gel filtration chromatography can be applied. In the final step, the fraction obtained by preparative chromatography may be further purified by means such as recrystallization or distillation. Each of the steps may be repeated two or more times under the same or different conditions as desired. Use of the means enables the compound of Formula (I) to be purified or isolated from the culture of the microorganism.

In the method for producing the compound of the present invention by the culturing means in this aspect, it is preferable that the compound of Formula (I) have the groups R', $R^2$, $R^3$, $R^4$, $R^5$ and $R^6$ exemplified above. In this case, the compounds of Formula (I) are compounds 40551-F, -D, -G, -H, -I, -K and -L produced by *Streptomyces* OPMA40551 strain. Use of the method of this aspect enables efficient production of the compound of Formula (I) corresponding to compounds 40551-F, -D, -G, -H, -I, -K and -L, particularly compound 40551-F.

By the method for producing the compound of the present invention by culturing means in this aspect, which has the above characteristics, a large amount of the compound of Formula (I) in one aspect of the present invention, which can be an active ingredient of a medicament, can be provided with a high purity and at low cost.

Another aspect of the present invention relates to a microorganism which is *Streptomyces* OPMA40551 strain (Accession No. NITE BP-02510) capable of producing the compound of Formula (I) in one aspect of the present invention, or a variant thereof. In this aspect, it is preferable that the compound of Formula (I) have the groups $R^1$, $R^2$, $R^3$, $R^4$, $R^5$ and $R^6$ exemplified above. Use of the microorganism of this aspect enables efficient production of the compound of Formula (I) corresponding to compounds 40551-F, -D, -G, -H, -I, -K and -L, particularly compound 40551-F.

<3. Medical Use>

The compound of Formula (I) in one aspect of the present invention has high antibacterial activity against nontuberculous mycobacteria such as *Mycobacterium avium* and *Mycobacterium intracellulare* which are causative bacteria of MAC infection. The compound of Formula (I) in one aspect of the present invention can also exhibit antibacterial activity against tuberculosis bacteria such as *Mycobacterium tuberculosis* and *Mycobacterium bovis*. Thus, another aspect of the present invention relates to a therapeutic agent for *Mycobacterium avium* complex infection (MAC infection), which comprises the compound of Formula (I) or a pharmaceutically acceptable salt thereof, or a pharmaceutically acceptable solvate thereof in one aspect of the present invention as an active ingredient. Still another aspect of the present invention relates to a therapeutic agent for tuberculosis bacteria such as *Mycobacterium tuberculosis* and *Mycobacterium bovis*, which comprises the compound of Formula (I) or a pharmaceutically acceptable salt thereof, or a pharmaceutically acceptable solvate thereof in one aspect of the present invention as an active ingredient. Still another aspect of the present invention relates to a medicament comprising the compound of Formula (I) or a salt thereof, or solvate thereof in one aspect of the present invention as an active ingredient.

The antibacterial activity of the compound of Formula (I) in one aspect of the present invention can be determined by, for example, but not limited to, calculating a minimum inhibitory concentration (MIC) value by a broth microdilution method in accordance with the following procedure. A bacterial suspension for inoculation is prepared from a stock bacterial suspension of arbitrary assay bacteria (e.g. *Mycobacterium avium*, *Mycobacterium intracellulare* or *Mycobacterium bovis*). To a 96-well microplate, a two-stage dilution series (e.g. a final concentration of 0.001 to 50 μg/mL) of a test compound sample prepared beforehand is dispensed at 5 μL/well. Next, the bacterial suspension for inoculation is added at 95 μL/well. The culture solution in the well is mixed, and the resulting mixture is cultured under appropriate conditions (e.g. at 37° C. for 30 to 120 hours). After the culture, observation is performed with naked eyes, or viable cells are stained with a MTT (3-(4,5-dimethyl-2-thiazolyl)-2,5-diphenyltetrazolium bromide) reagent to calculate a growth inhibition rate. On the basis of the calculated growth inhibition rate, the minimum concentration indicative of inhibition of bacteria is determined as a MIC value. On the basis of the growth inhibition rate and the MIC value determined in this manner, the antibacterial activity of the compound of Formula (I) in one aspect of the present invention can be evaluated.

In this aspect, the compound of Formula (I) in one aspect of the present invention has a MIC value determined in accordance with the procedure of, for example, 25 μg/mL or less, normally 1.0 μg/mL or less, typically 0.5 μg/mL or less against nontuberculous mycobacteria such as *Mycobacterium avium* and *Mycobacterium intracellulare* which are causative bacteria of MAC infection. The compound of Formula (I) in one aspect of the present invention has a MIC value determined in accordance with the procedure of, for example, 25 µg/mL or less, normally 5.0 µg/mL or less, typically 2.0 µg/mL or less against tuberculosis bacteria such as *Mycobacterium tuberculosis* and *Mycobacterium bovis*. By applying to a subject the compound of Formula (I) in one aspect of the present invention having a MIC value in the above-described range, infections with bacteria, such as MAC infection and tuberculosis, can be prevented or treated.

When the compound of Formula (I) in one aspect of the present invention is applied to a medical use, the compound of Formula (I) includes not only the compound itself, but also pharmaceutically acceptable salts of the compound, and pharmaceutically acceptable solvates thereof. Examples of preferred pharmaceutically acceptable salts of the compound of Formula (I) and pharmaceutically acceptable solvates thereof in one aspect of the present invention include, but are not limited to, the salts and solvates exemplified above. When the compound of Formula (I) is in the form of the above-described salt or solvate, the compound can be applied to a desired medical use without substantially reducing antibacterial activity against nontuberculous mycobacteria such as *Mycobacterium avium* and *Mycobacterium intracellulare* which are causative bacteria of MAC infection, and/or against tuberculosis bacteria.

When the compound of Formula (I) in one aspect of the present invention is applied to a medical use, the compound of Formula (I) includes the compound itself, but also prodrug forms of the compound. In the present specification, the "prodrug" means a compound which is transformed into a parent drug in vivo. Examples of the prodrug forms of the compound include, but are not limited to, amides of an amino group with any carboxylic acid when the amino group is present. When the compound of Formula (I) in one aspect of the present invention is the prodrug form, pharmacokinetics during administration of the prodrug form to a subject can be improved without substantially reducing the antibacterial activity of the compound of Formula (I) as a parent drug against nontuberculous mycobacteria such as *Mycobacterium avium* and *Mycobacterium intracellulare* which are causative bacteria of MAC infection, and/or against tuberculosis bacteria.

When the compound of Formula (I) in one aspect of the present invention is applied to a medical use, the compound may be used alone, or used in combination with one or more pharmaceutically acceptable components. The medicament of the present invention can be formulated according to a desired administration method into various dosage forms which are commonly used in the art. Thus, the medicament of this aspect can also be provided in the form of a pharmaceutical composition comprising the compound of Formula (I) or a pharmaceutically acceptable salt thereof, or a pharmaceutically acceptable solvate thereof in one aspect of the present invention, and one or more pharmaceutically acceptable carriers. The pharmaceutical composition of this aspect may contain one or more pharmaceutically acceptable media (e.g. solvents such as sterilized water or solutions such as physiological saline), excipients, binders, vehicles, solubilizing agents, preservatives, stabilizers, puffing agents, lubricants, surfactants, emulsifiers, oily liquids (e.g. vegetable oils), suspensions, buffers, soothing agents, antioxidants, sweetening agents and flavoring agents in addition to the above-described components.

The dosage form of the medicament comprising the compound of Formula (I) or a pharmaceutically acceptable salt thereof, or a pharmaceutically acceptable solvate thereof in one aspect of the present invention as an active ingredient is not particularly limited, and may be a formulation to be used for parenteral administration, or a formulation to be used for oral administration. The dosage form of the medicament of this aspect may be a formulation in a single-dosage form, or a formulation in a multi-dosage form. Examples of the formulation to be used for parenteral administration include injections such as sterile solutions or suspensions with water or other pharmaceutically acceptable media. Examples of components which can be mixed in the injection include, but are not limited to, vehicles such as isotonic liquids including physiological saline, glucose or other adjuvants (e.g. D-sorbitol, D-mannitol, D-mannose or sodium chloride), solubilizing agents such as alcohols (e.g. ethanol or benzyl alcohol), polyalcohols (e.g. polypropylene glycol or polyethylene glycol) and esters (e.g. benzyl benzoate), nonionic surfactants such as Polysolvate 80 (trademark) and polyoxyethylene hydrogenated castor oil, oily liquids such as sesame oil or soybean oil, buffers such as phosphate buffers or sodium acetate buffers, soothing agents such as benzalkonium chloride or procaine chloride, stabilizers such as human serum albumin or polyethylene glycol, preserving agents, and antioxidants. The prepared injection is filled into an appropriate vial (e.g. ample), and stored in an appropriate environment until it is used.

Examples of the formulation to be used for oral administration include tablets, pills, powders, capsules, microcapsules, elixirs, solutions, syrups, slurries and suspensions. As desired, the tablet may be formulated as a dosage form of a coated tablet coated with sugar or soluble film, a gelatin-encapsulated tablet, an enteric coated tablet or a film-coated tablet, or a dosage form of a double tablet or a multi-layer tablet.

Examples of components which can be mixed in tablets, capsules or the like include, but are not limited to, binders such as water, ethanol, propanol, single syrups, glucose solutions, carboxymethylcellulose, shellac, methylcellulose, potassium phosphate, polyvinyl pyrrolidone, gelatin, corn starch, gum tragacanth and gum Arabic; excipients such as crystalline cellulose, lactose, white soft sugar, sodium chloride, glucose, urea, starch, potassium carbonate, kaolin and silicic acid; disintegrants such as dry starch, sodium alginate, powdered agar, powdered laminaran, sodium hydrogencarbonate, potassium carbonate, polyoxyethylene sorbitan fatty acid esters, sodium lauryl sulfate, monoglyceride stearate, starch and lactose; disintegration inhibitors such as white soft sugar, stearin cacao butter and hydrogenated oil; absorption enhancers such as quaternary ammonium salt and sodium lauryl sulfate; moisturizing agents such as glycerin and starch; adsorbents such as starch, lactose, kaolin, bentonite and colloidal silicic acid; lubricants such as purified talc, stearic acid salts (e.g. magnesium stearate), powdered boric acid and polyethylene glycol; sweetening agents such as sucrose, lactose and saccharin; and flavoring agents such as peppermint, *Gaultheria* adenothrix oil and cherry. When the formulation is a capsule, the formulation may contain a liquid carrier such as a fat and oil.

The medicament comprising the compound of Formula (I) or a pharmaceutically acceptable salt thereof, or a pharmaceutically acceptable solvate thereof in one aspect of the present invention as an active ingredient can be formulated as a depot formulation. In this case, the medicament of this aspect in the dosage form of a depot formulation can be implanted under the skin or in the muscle, or administered by muscle injection. By applying the medicament of this aspect to a depot formulation, the antibacterial activity of the compound of Formula (I) in one aspect of the present invention against nontuberculous mycobacteria such as

*Mycobacterium avium* and *Mycobacterium intracellulare* which are causative bacteria of MAC infection, and/or against tuberculosis bacteria can be sustainably exhibited over a long period of time.

The medicament comprising the compound of Formula (I) or a pharmaceutically acceptable salt thereof, or a pharmaceutically acceptable solvate thereof in one aspect of the present invention as an active ingredient can be used in combination with one or more other pharmaceutically useful drugs. In this case, the medicament of this aspect is in the form of a combined medicament comprising the compound of Formula (I) or a pharmaceutically acceptable salt thereof, or a pharmaceutically acceptable solvate thereof in one aspect of the present invention, and the one or more other drugs. The combined medicament may be in the form of a pharmaceutical composition obtained by combining the compound of Formula (I) or a pharmaceutically acceptable salt thereof or a pharmaceutically acceptable solvate thereof in one aspect of the present invention with the one or more other drugs, or a pharmaceutical composition comprising the compound of Formula (I) or a pharmaceutically acceptable salt thereof or a pharmaceutically acceptable solvate thereof in one aspect of the present invention, which is used in combination with the one or more other drugs. When the medicament of this aspect is in the form of a combined medicament, the medicament may be provided in the form of a single formulation comprising the compound of Formula (I) or a pharmaceutically acceptable salt thereof, or a pharmaceutically acceptable solvate thereof in one aspect of the present invention, and one or more other drugs, or provided in the form of a medicament combination or kit comprising a plurality of formulations in which the compound, a pharmaceutically acceptable salt thereof or a pharmaceutically acceptable solvate thereof, and one or more other drugs are separately formulated. When the medicament is in the form of a medicament combination or kit, the formulations can be administered simultaneously or separately (e.g. successively).

The medicament comprising the compound of Formula (I) or a pharmaceutically acceptable salt thereof, or a pharmaceutically acceptable solvate thereof in one aspect of the present invention as an active ingredient can similarly prevent or treat an infection with one or more bacteria selected from the group consisting of nontuberculous mycobacteria and tuberculosis bacteria. Examples of the one or more bacteria include, but are not limited to, nontuberculous mycobacteria such as *Mycobacterium avium, Mycobacterium intracellulare* and *Mycobacterium smegmatis* (*M. smegmatis*), and tuberculosis bacteria such as *Mycobacterium tuberculosis* and *Mycobacterium bovis*. Examples of the infection with one or more bacteria include, but are not limited to, nontuberculous mycobacteria infections (e.g. MAC infection with *Mycobacterium avium* and *Mycobacterium intracellulare*), and tuberculosis. The infection with one or more bacteria is preferably MAC infection or tuberculosis, more preferably MAC infection. By administering the medicament of this aspect to a subject in need of prevention or treatment of the infection with one or more bacteria, a symptom, disease and/or disorder which is the infection can be prevented or treated.

The medicament comprising the compound of Formula (I) or a pharmaceutically acceptable salt thereof, or a pharmaceutically acceptable solvate thereof in one aspect of the present invention as an active ingredient can be applied to various subjects in need of prevention or treatment of a symptom, disease and/or disorder which is the infection with one or more bacteria (e.g. MAC infection or tuberculosis). The subject is preferably a subject or a patient of a human or a nonhuman mammal (e.g. warm-blooded animal such as pig, dog, bovine, rat, mouse, guinea pig, rabbit, chicken, sheep, cat, monkey, baboon or chimpanzee), a reptile (e.g. heterothermic animal such as frog, snake or lizard) or the like. By administering the medicament of this aspect to the subject, various symptoms, diseases and/or disorders which are infections with one or more bacteria in the subject can be prevented or treated.

In the present specification, the "prevention" means that occurrence (development or onset) of a symptom, disease and/or disorder is substantially prevented. In the present specification, the "treatment" means that a symptom, disease and/or disorder which has occurred (developed or emerged) is suppressed (e.g. progression is suppressed), alleviated, healed and/or cured.

The compound of Formula (I) in one aspect of the present invention can be used for preventing or treating various symptoms, diseases and/or disorders which is the above-described infection with one or more bacteria (e.g. MAC infection or tuberculosis) in a subject having the symptom, disease and/or disorder. Thus, the medicament of this aspect is preferably a medicament for use in preventing or treating a symptom, disease and/or disorder which is the above-described infection with one or more bacteria, more preferably a medicament for use in preventing or treating a symptom, disease and/or disorder which is an infection with one or more bacteria selected from the group consisting of MAC infection and tuberculosis. By using the medicament of this aspect for preventing or treating the symptom, disease and/or disorder which is the infection with one or more bacteria described above, the symptom, disease and/or disorder can be prevented or treated with the aid of the antibacterial activity of the compound of Formula (I) in one aspect of the present invention.

The compound of Formula (I) in one aspect of the present invention can be used for preventing or treating various symptoms, diseases and/or disorders which is the above-described infection with one or more bacteria (e.g. MAC infection or tuberculosis) in a subject having the symptom, disease and/or disorder. Thus, another aspect of the present invention is a method for preventing or treating a symptom, disease and/or disorder which is the above-described infection with one or more bacteria, which comprises administering an effective amount of the compound of Formula (I) or a pharmaceutically acceptable salt thereof, or a pharmaceutically acceptable solvate thereof in the present invention to a subject in need of prevention or treatment of the symptom, disease and/or disorder. The symptom, disease and/or disorder which is the infection with one or more bacteria is preferably one or more symptoms, disease and/or disorders selected from the group consisting of MAC infection and tuberculosis. By administering the compound of Formula (I) in one aspect of the present invention to a subject in need of prevention or treatment of a symptom, disease and/or disorder which is the infection with one or more bacteria, the symptom, disease and/or disorder can be prevented or treated with the aid of the antibacterial activity of the compound of Formula (I) in one aspect of the present invention.

Another aspect of the present invention is the compound of Formula (I) or a pharmaceutically acceptable salt thereof, or a pharmaceutically acceptable solvate thereof in one aspect of the present invention for use in preventing or treating a symptom, disease and/or disorder which is the above-described infection with one or more bacteria (e.g. MAC infection or tuberculosis). Another aspect of the present invention is use of the compound of Formula (I) or a pharmaceutically acceptable salt thereof, or a pharmaceutically acceptable solvate thereof in one aspect of the present invention in the manufacture of a medicament for preventing or treating a symptom, disease and/or disorder which is the above-described infection with one or more bacteria (e.g. MAC infection or tuberculosis). The symptom, disease and/or disorder which is the infection with one or more bacteria is preferably one or more infectious symptoms, diseases and/or disorders selected from the group consisting of MAC infection and tuberculosis. By using the compound of Formula (I) in one aspect of the present invention or the medicament for preventing or treating a symptom, disease and/or disorder which is the infection with one or more bacteria, the symptom, disease and/or disorder can be prevented or treated with the aid of the antibacterial activity of the compound of Formula (I) in one aspect of the present invention.

When the medicament comprising the compound of Formula (I) or a pharmaceutically acceptable salt thereof, or a pharmaceutically acceptable solvate thereof in one aspect of the present invention as an active ingredient is administered to a subject, particularly a human patient, an attending doctor should definitely determine an accurate dosage and regimen (e.g. dose, administration frequency and/or administration route) with consideration given to a therapeutically effective dose, administration frequency, administration route and the like in light of many factors such as the age and sex of a subject, accurate conditions (e.g. severity) of a symptom, disease and/or disorder to be prevented or treated, and the administration route. Thus, the compound of Formula (I) which is an active ingredient in the medicament of this aspect is administered to a subject with a therapeutically effective amount and frequency. For example, when the medicament of this aspect is administered to a human patient, the dose of the compound of Formula (I) which is an active ingredient is normally in the range of 0.001 to 100 mg/kg of body weight per one administration, typically in the range of 0.01 to 10 mg/kg of body weight per one administration, particularly in the range of 0.1 to 10 mg/kg of body weight per one administration. The administration frequency of the medicament of this aspect may be 1 or more per day, or 1 in several days. The administration route of the medicament of this aspect is not particularly limited, and the medicament may be administered orally, or administered parenterally (e.g. intrarectally, transmucosally, enterally, intramuscularly, subcutaneously, in the bone marrow, intrathecally, directly in the ventricle, intravenously, intravitreally, intraperitoneally, intranasally or in the eye) one time or two or more times. By using the medicament of this aspect with the above-described dosage and regimen, the symptom, disease and/or disorder which is the infection with one or more bacteria can be prevented or treated with the aid of the antibacterial activity of the compound of Formula (I) in one aspect of the present invention.

EXAMPLES

Hereinafter, the present invention will be described in more detail by way of Examples, but the technical scope of the present invention is not limited to these Examples.
<I. Production of Novel Compound by Culturing Means>
[Separation of OPMA40551 Strain]

The OPMA40551 strain is an actinomycete isolated in Japan. The morphological characteristics, culture properties and physiological properties of OPMA40551 strain were compared with those of known bacterial species. The results revealed that this strain was a novel strain belonging to *Streptomyces*. The strain was named OPMA40551 strain. The strain was internationally deposited as OPMA40551 (Accession No. NITE BP-02510) under the Budapest Treaty on Jul. 18, 2017 at National Institute of Technology and Evaluation, Patent Microorganisms Depository Center (#122, 2-5-8, Kazusakamatari, Kisarazu-shi, Chiba, 292-0818 Japan). The mycological properties of OPMA40551 strain are as follows.
1. Morphological Characteristics The OPMA40551 strain was successfully grown on a medium such as a nutrient agar medium such as ISP2 medium. A colony grown on ISP2 medium at 25° C. under aerobic conditions for 10 days was observed with a microscope, and the result showed that basic viable mycelia were filamentous, aerial mycelia were sparsely formed, and spore formation did not occur. The upper surface and the back surface were creamy, and coloring of the medium by soluble pigments or melanoid pigments did not occur.
2. Culture Properties The OPMA40551 strain was successfully grown by performing static culture at 25° C. under aerobic conditions for 5 to 10 days on a medium such as a nutrient agar medium such as ISP2 medium.
3. Physiological Properties Optimum growth conditions for OPMA40551 strain were aerobic conditions with a temperature of 25° C. Conditions enabling growth of this strain were such that static culture was performed under aerobic conditions at a pH of 6 to 8 and a temperature of 15 to 37° C. for a culture period of 5 to 10 days.

Production Example I-1: Culture of OPMA40551 Strain (1)

Three bacteria-originating agar pieces of OPMA40551 strain cultured in sea-prepared ISP2 agar medium (yeast extract: 0.20% (DIFCO), malt extract: 0.50% (DIFCO), glucose: 0.20% (Wako Pure Chemical Industries, Ltd.), Artificial Sea Water Marine Art SF-1: 1.92% (Tomita Pharmaceutical Co., Ltd.), tap water: 1.0 L, natural sea water: 1.0 L (Deep Ocean), agar: 1.0% (SSK Sales Co. Ltd.), pH: adjusted to 7.3) were inoculated in a 500 mL conical flask containing 100 mL of SPY medium (soluble starch: 1.0% (Wako Pure Chemical Industries, Ltd.), peptone: 0.50% (DIFCO), yeast extract: 0.25% (DIFCO), natural sea water (Deep Ocean), pH: not adjusted). This strain was cultured with a rotary shaker (180 rpm) at 27° C. for 2 days. Thereafter, the resulting culture broth was inoculated in an amount of 1% by volume in 500 mL conical flasks to which 3 L of SPY medium had been dispensed. This strain was subjected to shaking culture at 27° C. for 7 days.

Production Example I-2: Purification of Novel Compound from Culture Broth of OPMA40551 Strain (1)

Ethyl acetate (3 L) was added to the culture broth (3 L) obtained in Production Example I-1, and the resulting mixture was ultrasonically crushed for 1 hour. The culture broth was subjected to suction filtration to remove crushed mycelia. The resulting ethyl acetate layer was dried under reduced pressure to obtain a crude extract (297.8 mg). The crude extract was separated by ODS column chromatography (Senshu Scientific Co., Ltd., 15 g) with 20%, 40%, 60%, 80% and 100% aqueous methanol solutions (100 mL each) used as developing solvents. The eluates were fractionated to 100 mL. The 80% aqueous methanol solution fraction was concentrated to obtain a yellow oily substance (18.8 mg). This substance was dissolved in a small amount of methanol, and the resulting solution was further separated by preparative HPLC (column: PEGASIL ODS SP100, 20 φ×250 mm, Senshu Scientific Co., Ltd.). A 20 to 45% aqueous acetonitrile solution (containing 0.05% trifluoroacetic acid) was used as a mobile phase at a flow rate of 6 mL/min under a gradient condition for 40 minutes, and an absorption at 210 nm (UV) was monitored. A peak showing activity was observed at a retention time of 24 minutes, the solution was fractionated at this peak, and the fractionated solution was freeze-dried to isolate compound 40551-F as a colorless oily substance with a yield of 1.4 mg. The chemical structure of compound 40551-F (N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidine-4-yl)-3-methylbuta-2-enamide) is shown below.

[Formula 10]

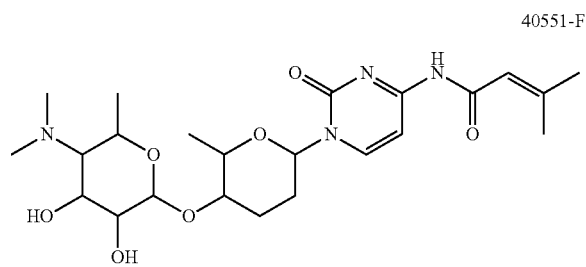

40551-F

[Compound 40551-F]
(1) Property: colorless and oily
(2) Molecular formula: $C_{23}H_{36}N_4O_7$
HRESI-MS (m/z) $[M+H]^+$ calculated value: 481.2662, measured value: 481.2661
(3) Molecular weight: 480
ESI-MS (m/z) $[M+H]^+=481$, $[M+Na]^+=503$ were observed
(4) Ultraviolet region absorption spectrum: measured in methanol solution, $\lambda_{max}$ (MeOH, ε): 209 nm (8215), 265 nm (13895), 300 nm (5960)
(5) Infrared region absorption spectrum: measured by potassium bromide tablet method, $v_{max}$ 3414, 2934, 1680, 1640, 1489, 1205 $cm^{-1}$, etc.
(6) Specific rotation: $[\alpha]_D^{24}+74.3°$ (c=0.1, methanol)
(7) Solubility in solvent: soluble in methanol, DMSO, etc.
(8) Proton and carbon nuclear magnetic resonance spectrum: the hydrogen chemical shift (ppm) and the carbon chemical shift (ppm) measured in heavy methanol with 400 MHz Nuclear Magnetic Resonance Spectrometer manufactured by Agilent Technologies are as follows: $\delta_H$: 1.37 (3H), 1.45 (3H), 1.68 (2H), 1.96 (3H), 2.14 (1H), 2.22 (3H), 2.38 (1H), 3.00 (6H), 3.11 (1H), 3.43 (1H), 3.55 (1H), 3.75 (1H), 3.96 (1H), 4.09 (1H), 5.01 (1H), 5.76 (1H), 5.94 (1H), 7.54 (1H), 8.08 (1H) ppm $\delta_C$: 19.0, 19.2, 20.5, 27.8, 28.0, 30.9, 42.3, 42.3, 64.0, 67.9, 71.9, 73.9, 76.5, 78.2, 84.5, 96.6, 98.4, 118.8, 145.8, 157.5, 159.7, 164.8, 167.7 ppm.

Production Example I-3: Culture of OPMA40551 Strain (2)

Three bacteria-originating agar pieces of OPMA40551 strain cultured in sea-prepared ISP2 agar medium (yeast extract: 0.20% (DIFCO), malt extract: 0.50% (DIFCO), glucose: 0.20% (Wako Pure Chemical Industries, Ltd.), Artificial Sea Water Marine Art SF-1: 1.92% (Tomita Pharmaceutical Co., Ltd.), tap water: 1.0 L, natural sea water: 1.0 L (Deep Ocean), agar: 1.0% (SSK Sales Co. Ltd.), pH: adjusted to 7.3) were inoculated in a 500 mL conical flask containing 100 mL of SPY medium. This strain was cultured with a rotary shaker (180 rpm) at 27° C. for 2 days. Thereafter, the resulting culture broth was inoculated in an amount of 1% by volume in each of thirty 500 mL conical flasks to which 3 L of SPY medium had been dispensed with each conical flask containing 100 mL of SPY medium. This strain was subjected to shaking culture at 27° C. for 11 days.

Production Example I-4: Purification of Novel Compound from Culture Broth of OPMA40551 Strain (2)

The culture broth (3 L) obtained in Production Example I-3 was dispensed into six equal parts to six 500 mL plastic centrifuging tubes, respectively. Each of the dispensed culture broths was centrifuged under condition of 8,000 rpm at 4° C. for 20 minutes, and the supernatant was collected. The pH of the supernatant at this time was measured, and the result showed that the pH was 10. Ethyl acetate (3 L) was added to the supernatant to obtain an ethyl acetate layer. The resulting ethyl acetate layer was dried under reduced pressure to obtain a crude extract (164.4 mg). The crude extract was separated by ODS column chromatography (Fuji Silysia Chemical Ltd., 8.2 g) with 20%, 40%, 60%, 70%, 80% and 100% aqueous methanol solutions used as developing solvents. The eluates were fractionated to 60 mL under respective conditions. The 70% aqueous methanol solution fraction and the 80% aqueous methanol solution fraction were concentrated to obtain a yellow oily substance (21.5 mg) and a white oily substance (6.0 mg), respectively. These substances were each dissolved in a small amount of methanol, and the resulting solutions were separated by preparative HPLC (column: PEGASIL ODS SP100, 20 φ×250 mm, Senshu Scientific Co., Ltd.). For the 70% aqueous methanol solution fraction, a 20 to 45% aqueous acetonitrile solution (containing 0.05% trifluoroacetic acid) was used as a mobile phase at a flow rate of 6 mL/min under a gradient condition for 50 minutes, and an absorption at 210 nm (UV) was monitored. Peaks showing activity were observed at retention times of 26, 29, 32 and 34 minutes, the solutions were fractionated at these peaks, the solvents of the fractions were removed under reduced pressure, and the fractionated solutions were then freeze-dried to isolate compounds 40551-D, 40551-I, 40551-K and 40551-L with yields of 1.65 mg, 1.61 mg, 2.06 mg and 0.93 mg, respectively. For the 80% aqueous methanol solution fraction, a 30 to 60% aqueous acetonitrile solution (containing 0.05% trifluoroacetic acid) was used as a mobile phase at a flow rate of 6 mL/min under a gradient condition for 40 minutes, and an absorption at 260 nm (UV) was monitored. A peak showing activity was observed at a retention time of 21 minutes, the solution was fractionated at this peak, the solvent of the fraction was removed under reduced pressure, and the fractionated solution was then freeze-dried to isolate compound 40551-G with a yield of 0.80 mg.

The chemical structure of compound 40551-D (N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-isobutylamide) is shown below.

[Formula 11]

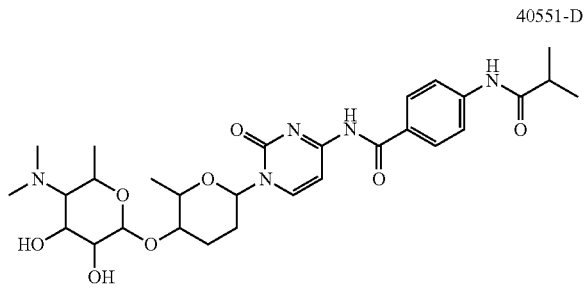

40551-D

[Compound 40551-D]
(1) Property: amorphous
(2) Molecular formula: $C_{29}H_{41}N_5O_8$
HRESI-MS (m/z) [M+Na]$^+$ calculated value: 610.2853, measured value: 610.2853
(3) Molecular weight: 587
ESI-MS (m/z) [M+H]$^+$=588, [M+Na]$^+$=610 were observed
(4) Ultraviolet region absorption spectrum: measured in methanol solution, $\lambda_{max}$ (MeOH, ε): 303 nm (15458)
(5) Infrared region absorption spectrum: measured by potassium bromide tablet method, $\nu_{max}$ 3304, 2978, 2937, 1680, 1486, 1204 cm$^{-1}$, etc.
(6) Specific rotation: $[\alpha]_D^{24}$+75.4° (c=0.1, methanol)+75.4.
(7) Solubility in solvent: soluble in methanol, DMSO, etc.
(8) Proton and carbon nuclear magnetic resonance spectrum: the hydrogen chemical shift (ppm) and the carbon chemical shift (ppm) measured in heavy methanol with 600 MHz Nuclear Magnetic Resonance Spectrometer manufactured by Bruker are as follows: $\delta_H$: 1.21 (6H), 1.39 (3H), 1.46 (3H), 1.70 (2H), 2.18 (1H), 2.39 (1H), 2.67 (1H), 3.00 (6H), 3.12 (1H), 3.43 (1H), 3.55 (1H), 3.76 (1H), 3.96 (1H), 4.09 (1H), 5.02 (1H), 5.78 (1H), 7.62 (1H), 7.77 (2H), 7.96 (2H), 8.17 (1H) ppm
$\delta_C$: 19.0, 19.2, 19.8, 19.8, 28.3, 30.9, 37.2, 42.4, 42.4, 64.0, 67.9, 71.9, 73.9, 76.5, 78.2, 84.6, 96.6, 98.8, 120.3, 120.3, 129.2, 130.3, 130.3, 144.8, 146.2, 157.3, 164.8, 168.4, 178.9 ppm.

The chemical structure of compound 40551-G ((E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl-4-methylhex-2-enamide) is shown below.

[Formula 12]

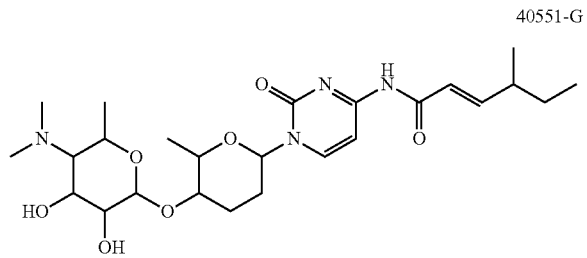

40551-G

[Compound 40551-G]
(1) Property: amorphous
(2) Molecular formula: $C_{25}H_{40}N_4O_7$
HRESI-MS (m/z) [M+Na]$^+$ calculated value: 509.2975, measured value: 509.2969
(3) Molecular weight: 508
ESI-MS (m/z) [M+H]$^+$=509, [M+Na]$^+$=531 were observed
(4) Ultraviolet region absorption spectrum: measured in methanol solution, $\lambda_{max}$ (MeOH, ε): 261 nm (5913), 301 nm (2030)
(5) Infrared region absorption spectrum: measured by potassium bromide tablet method, $\nu_{max}$ 3415, 2933, 1681, 1492, 1205 cm$^{-1}$, etc.
(6) Specific rotation: $[\alpha]_D^{24}$+59.8 (c=0.08, methanol)
(7) Solubility in solvent: soluble in methanol, DMSO, etc.
(8) Proton and carbon nuclear magnetic resonance spectrum: the hydrogen chemical shift (ppm) and the carbon chemical shift (ppm) measured in heavy methanol with 600 MHz Nuclear Magnetic Resonance Spectrometer manufactured by Bruker are as follows: $\delta_H$: 0.92 (3H), 1.09 (3H), 1.38 (3H), 1.44 (3H), 1.46 (2H), 1.68 (2H), 2.15 (1H), 2.30 (1H), 2.39 (1H), 2.96 (6H), 3.03 (1H), 3.43 (1H), 3.54 (1H), 3.75 (1H), 3.95 (1H), 4.07 (1H), 5.00 (1H), 5.76 (1H), 6.14 (1H), 6.97 (1H), 7.55 (1H), 8.11 (1H) ppm
$\delta_C$: 12.0, 19.1, 19.2, 19.3, 28.1, 29.9, 30.9, 39.5, 42.3, 42.3, 64.3, 68.1, 71.9, 73.9, 76.4, 78.2, 84.6, 96.6, 98.6, 122.9, 146.0, 155.9, 157.4, 164.7, 167.7 ppm.

The chemical structure of compound 40551-I ((E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-2-methylbuta-2-enamide) is shown below.

[Formula 13]

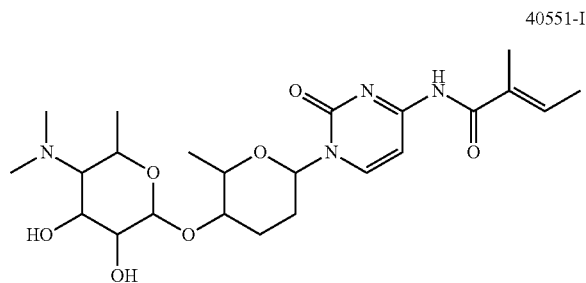

40551-I

[Compound 40551-I]
(1) Property: amorphous
(2) Molecular formula: $C_{23}H_{36}N_4O_7$
HRESI-MS (m/z) [M+Na]$^+$ calculated value: 503.2482, measured value: 503.2467
(3) Molecular weight: 480
ESI-MS (m/z) [M+H]$^+$=481, [M+Na]$^+$=503 were observed
(4) Ultraviolet region absorption spectrum: measured in methanol solution, $\lambda_{max}$ (MeOH, ε): 258 nm (4692), 301 nm (2538)
(5) Infrared region absorption spectrum: measured by potassium bromide tablet method, $\nu_{max}$ 3381, 2935, 1681, 1486, 1204 cm$^{-1}$, etc.
(6) Specific rotation: $[\alpha]_D^{25}$+47.6° (c=0.1, methanol)
(7) Solubility in solvent: soluble in methanol, DMSO, etc.
(8) Proton and carbon nuclear magnetic resonance spectrum: the hydrogen chemical shift (ppm) and the carbon chemical shift (ppm) measured in heavy methanol with 600 MHz Nuclear Magnetic Resonance Spectrometer manufactured by Bruker are as follows: $\delta_H$: 1.38 (3H), 1.45 (3H), 1.68 (2H), 1.87 (3H), 1.89 (3H), 2.15 (1H), 2.38 (1H), 2.99 (6H), 3.10 (1H), 3.43 (1H), 3.55 (1H), 3.75 (1H), 3.95 (1H), 4.08 (1H), 5.00 (1H), 5.76 (1H), 6.65 (1H), 7.48 (1H), 8.11 (1H) ppm $\delta_C$: 12.2, 14.5, 19.0, 19.2, 28.0, 30.9, 42.4, 42.4, 64.1, 68.0, 71.9, 73.9, 76.4, 78.2, 84.6, 96.6, 98.4, 133.5, 136.2, 146.0, 157.0, 164.8, 170.8 ppm.

The chemical structure of compound 40551-K (N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-3-butanamide is shown below.

[Formula 14]

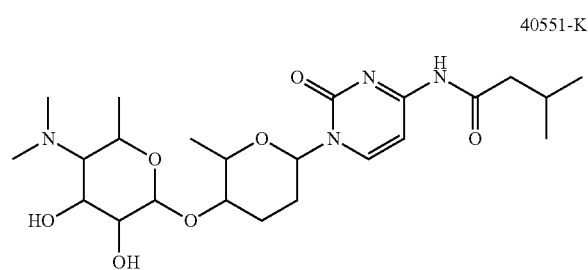

40551-K

[Compound 40551-K]

(1) Property: amorphous (2) Molecular formula: $C_{23}H_{38}N_4O_7$

HRESI-MS (m/z) $[M+H]^+$ calculated value: 483.2819, measured value: 483.2819

(3) Molecular weight: 482

ESI-MS (m/z) $[M+H]^+=483$, $[M+Na]^+=505$ were observed (4) Ultraviolet region absorption spectrum: measured in methanol solution, $\lambda_{max}$ (MeOH, ε): 249 nm (5652), 295 nm (2986)

(5) Infrared region absorption spectrum: measured by potassium bromide tablet method, $\nu_{max}$ 3422, 2963, 2937, 1678, 1491, 1203 cm$^{-1}$, etc.

(6) Specific rotation: $[\alpha]_D^{25}$ +64.7° (c=0.1, methanol)

(7) Solubility in solvent: soluble in methanol, DMSO, etc.

(8) Proton and carbon nuclear magnetic resonance spectrum: the hydrogen chemical shift (ppm) and the carbon chemical shift (ppm) measured in heavy methanol with 600 MHz Nuclear Magnetic Resonance Spectrometer manufactured by Bruker are as follows: $\delta_H$: 1.01 (6H), 1.39 (3H), 1.48 (3H), 1.70 (2H), 2.16 (1H), 2.17 (1H), 2.34 (2H), 2.40 (1H), 3.02 (6H), 3.13 (1H), 3.44 (1H), 3.57 (1H), 3.76 (1H), 3.98 (1H), 4.10 (1H), 5.03 (1H), 5.78 (1H), 7.51 (1H), 8.12 (1H) ppm $\delta_C$: 19.0, 19.2, 22.6, 22.6, 27.0, 28.0, 30.9, 42.3, 42.3, 47.2, 64.0, 67.9, 72.0, 73.8, 76.5, 78.2, 84.6, 96.6, 98.4, 146.2, 157.4, 164.3, 175.3 ppm.

The chemical structure of compound 40551-L ((E)-N-(1-(5-((5-(dimethylamino)-3,4-dihydroxy-6-methyltetrahydro-2H-pyran-2-yl)oxy)-6-methyltetrahydro-2H-pyran-2-yl)-2-oxo-1,2-dihydropyrimidin-4-yl)-4-methylpenta-2-enamide) is shown below.

[Formula 15]

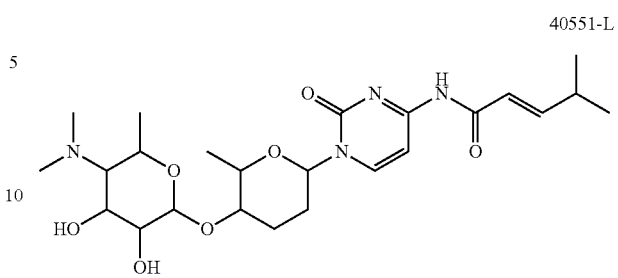

40551-L

[Compound 40551-L]

(1) Property: amorphous (2) Molecular formula: $C_{24}H_{38}N_4O_7$

HRESI-MS (m/z) $[M+H]^+$ calculated value: 495.2819, measured value: 495.2814

(3) Molecular weight: 494

ESI-MS (m/z) $[M+H]^+=495$, $[M+Na]^+=517$ were observed (4) Ultraviolet region absorption spectrum: measured in methanol solution, $\lambda_{max}$ (MeOH, ε): 260 nm (12391), 302 nm (5365)

(5) Infrared region absorption spectrum: measured by potassium bromide tablet method, $\nu_{max}$ 3408, 2965, 2934, 1678, 1492, 1203 cm$^{-1}$, etc.

(6) Specific rotation: $[\alpha]_D^{25}$ +65.5° (c=0.05, methanol)

(7) Solubility in solvent: soluble in methanol, DMSO, etc.

(8) Proton and carbon nuclear magnetic resonance spectrum: the hydrogen chemical shift (ppm) and the carbon chemical shift (ppm) measured in heavy methanol with 600 MHz Nuclear Magnetic Resonance Spectrometer manufactured by Bruker are as follows: $\delta_H$: 1.11 (6H), 1.37 (3H), 1.46 (3H), 1.69 (2H), 2.15 (1H), 2.39 (1H), 2.53 (1H), 3.00 (6H), 3.11 (1H), 3.43 (1H), 3.55 (1H), 3.75 (1H), 3.96 (1H), 4.09 (1H), 5.02 (1H), 5.77 (1H), 6.14 (1H), 7.05 (1H), 7.56 (1H), 8.12 (1H) ppm $\delta_C$: 19.0, 19.2, 21.6, 21.6, 28.0, 30.9, 32.3, 42.4, 42.4, 64.0, 67.9, 72.0, 73.9, 76.5, 78.2, 84.6, 96.6, 98.6, 121.8, 146.0, 156.9, 156.9, 164.7, 167.6 ppm.

Production Example I-5: Culture of OPMA40551 Strain (3)

Three bacteria-originating agar pieces of OPMA40551 strain cultured in sea-prepared ISP2 agar medium (yeast extract: 0.20% (DIFCO), malt extract: 0.50% (DIFCO), glucose: 0.20% (Wako Pure Chemical Industries, Ltd.), Artificial Sea Water Marine Art SF-1: 1.92% (Tomita Pharmaceutical Co., Ltd.), tap water: 1.0 L, natural sea water: 1.0 L (Deep Ocean), agar: 1.0% (SSK Sales Co. Ltd.), pH: adjusted to 7.3) were inoculated in a 500 mL conical flask containing 100 mL of SPY medium. This strain was cultured with a rotary shaker (180 rpm) at 27° C. for 2 days. Thereafter, the resulting culture broth was inoculated in an amount of 1% by volume in each of thirty 500 mL conical flasks to which 3 L of SPY medium had been dispensed with each conical flask containing 100 mL of SPY medium. This strain was subjected to shaking culture at 27° C. for 7 days.

Production Example I-6: Purification of Novel Compound from Culture Broth of OPMA40551 Strain (3)

Amberlite XAD7HP resin (SIGMA, 150 mL) was added to the culture broth (3 L) obtained in Production Example I-5. The mixture was stirred with a propeller under conditions of 300 rpm for 3 hours. Thereafter, mycelia and the resin were collected by suction filtration. The mycelia and the resin were transferred into a stainless tube, and acetone (2 L) was then added. The mixture was stirred with a propeller under conditions of 300 rpm for 3 hours. Thereafter, the mycelia and the resin were removed by suction filtration, and the filtrate was collected. The filtrate was dried under reduced pressure to obtain a crude extract (2.99 g). The crude extract was separated by ODS column chromatography (Fuji Silysia Chemical Ltd., 100 g) with 20%, 40%, 60%, 70%, 80% and 100% aqueous methanol solutions used as developing solvents. The eluates were fractionated to 500 mL under respective conditions. The 70% aqueous methanol solution was concentrated to obtain a yellow oily substance (248.4 mg). This substance was dissolved in a small amount of methanol, and the resulting solution was separated by preparative HPLC (column: PEGASIL ODS SP100, 20 φ×250 mm, Senshu Scientific Co., Ltd.). A 20 to 45% aqueous acetonitrile solution (containing 0.05% trifluoroacetic acid) was used as a mobile phase at a flow rate of 6 mL/min under a gradient condition for 50 minutes, and an absorption at 210 nm (UV) was monitored. A peak showing activity was observed at a retention time of 13 minutes, the solution was fractionated at this peak, the solvent of the fraction was removed under reduced pressure, and the fractionated solution was then freeze-dried to isolate compound 40551-H with a yield of 13.7 mg. The chemical structure of compound 40551-H (1-(5-((5-(dimethylamino)-3,4-dihydroxy-6-methyltetrahydro-2H-pyran-2-yl)oxy)-6-methyltetrahydro-2H-pyran-2-yl)-4-(4-(hydroxymethyl)-2,2,4-trimethyl-5-oxoimidazolidin-1-yl)pyrimidine-2(1H)-one) is shown below.

(8) Proton and carbon nuclear magnetic resonance spectrum: the hydrogen chemical shift (ppm) and the carbon chemical shift (ppm) measured in heavy methanol with 400 MHz Nuclear Magnetic Resonance Spectrometer manufactured by Agilent Technologies are as follows: $\delta_H$: 1.39 (3H), 1.48 (3H), 1.55 (3H), 1.68 (3H), 1.70 (2H), 1.72 (3H), 2.18 (1H), 2.39 (1H), 3.00 (6H), 3.12 (1H), 3.43 (1H), 3.55 (1H), 3.61 (1H), 3.78 (1H), 3.96 (1H), 3.98 (1H), 4.09 (1H), 5.02 (1H), 5.78 (1H), 7.49 (2H), 7.62 (1H), 8.10 (2H), 8.19 (1H) ppm $\delta_C$: 19.0, 19.2, 20.6, 27.8, 28.0, 29.1, 30.9, 42.4, 42.4, 64.0, 65.5, 66.8, 67.9, 71.9, 73.9, 76.5, 78.2, 79.2, 84.7, 96.6, 98.8, 130.6, 130.6, 130.9, 130.9, 135.4, 140.9, 146.4, 157.2, 164.7, 168.3, 173.7 ppm.

<II. Pharmacological Test of Novel Compound>
[Test II-1: Evaluation Test on Antibacterial Activity Against *Mycobacterium Avium* Complex]

6 mL of 7H9 liquid medium (Middlebrook 7H9 broth 0.5% (DIFCO), bovine serum albumin 5.0% (SIGMA), glucose 2.0% (Wako Pure Chemical Industries, Ltd.) and sodium chloride 0.85% (Kanto Chemical Co., Inc.)) containing 0.05% Tween80 (Wako Pure Chemical Industries, Ltd.) was put in a cell culturing flask T25 (Corning incorporated). To this flask was added 200 μL of a glycerol stored bacterial suspension of *Mycobacterium avium* (JCM15430, given by Institute of Physical and Chemical Research, Microbe Division) or 120 μL of a glycerol stored bacterial suspension of *Mycobacterium intracellulare* (JCM6384, given by Institute of Physical and Chemical Research, Microbe Division). The *Mycobacterium avium* was statically cultured at 37° C. for 96 hours, and the *Mycobacterium intracellulare* was statically cultured at 37° C. for 72 hours. The cultured bacterial suspension was diluted with the medium by 200 times for the *Mycobacterium avium* and by 600 times for the *Mycobacterium intracellulare* to prepare bacterial suspensions for inoculation (equivalent to 4×10^6 CFU/mL). The minimum inhibitory concentration (MIC) of each bacterial suspension was measured by carrying out a broth microdilution method in accordance with the following procedure. To a 96-well microplate, a two-stage dilution series (a final concentration of 0.001 to 50 μg/mL) of a test compound sample prepared beforehand was dispensed at 5 μL/well. Next, the bacterial suspension for inoculation was added at 95 μL/well. The culture solution in the well was mixed, and the resulting mixture cultured at 37° C. for 120 hours. After the culture, MTT reagent (SIGMA) was added at 5 μL/well, and the resulting mixture was cultured at 37° C. for 16 hours. Thereafter, a cytolytic buffer (dimethylfor-

[Formula 16]

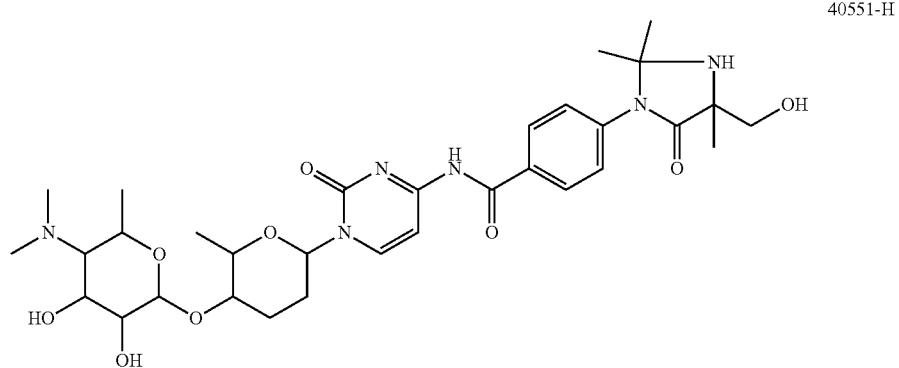

40551-H

[Compound 40551-H]
(1) Property: white and amorphous
(2) Molecular formula: $C_{32}H_{46}N_6O_9$
HRESI-MS (m/z) [M+H]$^+$ calculated value: 659.3405, measured value: 659.3385
(3) Molecular weight: 658
ESI-MS (m/z) [M+H]$^+$=659 was observed
(4) Ultraviolet region absorption spectrum: measured in methanol solution, $\lambda_{max}$ (MeOH, ε): 283 nm (13003)
(5) Infrared region absorption spectrum: measured by potassium bromide tablet method, $\nu_{max}$ 3283, 2984, 2935, 1679, 1487, 1202 cm$^{-1}$, etc.
(6) Specific rotation: $[\alpha]_H^{24}$+74.2° (c=0.1, methanol)
(7) Solubility in solvent: soluble in methanol, DMSO, etc.

mamide: 40.0% (nacalai tesque), acetic acid: 2.0% (Kanto Chemical Co., Inc.), sodium dodecyl sulfate: 20.0% (Wako Pure Chemical Industries, Ltd.), hydrochloric acid: 0.03 N (Kanto Chemical Co., Inc.)) at 95 μL/well, and the resulting mixture was shaken for 1 hour. For the culture solution in each well, the absorbance was measured at 570 nm, the growth inhibition rate was then calculated, and the minimum concentration indicative of inhibition of growth of 90% or more of bacteria was defined as a MIC value. Compounds 40551-F, -D, -G, -H, -I, -K and -L were used as test compounds, and ethambutol which is a known drug that is used for treatment of MAC infection was used as a comparative compound.

[Test II-2: Evaluation Test on Antibacterial Activity against Other Nontuberculous Mycobacteria and Tuberculosis Bacteria]

A test against *Mycobacterium smegmatis* as other nontuberculous mycobacteria was conducted in accordance with the following procedure. 6 mL of 7H9 liquid medium containing 0.5% Tween80 (Wako Pure Chemical Industries, Ltd.) was put in a cell culturing flask T25 (Corning incorporated). In this flask, a glycelol stored bacterial suspension of *Mycobacterium smegmatis* (MC²155, acquired from American Type Culture Collection) was inoculated with one platinum loop, and statically cultured at 37° C. for 30 hours. The cultured bacterial suspension was then diluted by 200 times with the medium to prepare a bacterial suspension for inoculation (equivalent to $8\times10^6$ CFU/mL). The MIC of the bacterial suspension was measured by carrying out a broth microdilution method in the same procedure as in Test II-1. The bacterial suspension was cultured under conditions of 37° C. for 30 hours, and the MIC value was determined by observing growth of bacteria with the naked eye.

A test against *Mycobacterium bovis* was conducted in accordance with the following procedure. 6 mL of 7H9 liquid medium containing 0.5% Tween80 (Wako Pure Chemical Industries, Ltd.) was put in a cell culturing flask T25 (Corning incorporated). 500 μL of a glycelol stored bacterial suspension of *Mycobacterium bovis* (BCG Pasteur, acquired from American Type Culture Collection) was added to this flask, and statically cultured at 37° C. for 120 hours. The cultured bacterial suspension was then diluted by 500 times with the medium to prepare a bacterial suspension for inoculation (equivalent to $8\times10^6$ CFU/mL). The MIC of the bacterial suspension was measured by carrying out a broth microdilution method in the same procedure as in Test II-1.

[Results of Pharmaceutical Test II]

Table 1 shows the antibacterial activities of the test compounds against the test bacteria.

The present invention is not limited to the above Examples, and include various modifications. For example, the above Examples are described in detail for easily understanding the present invention, and are not limited to those including all of the configurations described. The configuration of each Example can be partially provided with other configurations, omitted and/or replaced.

All publications, patents and patent applications cited in the present application are incorporated herein by reference in their entirety.

The invention claimed is:

1. A compound of Formula (I):

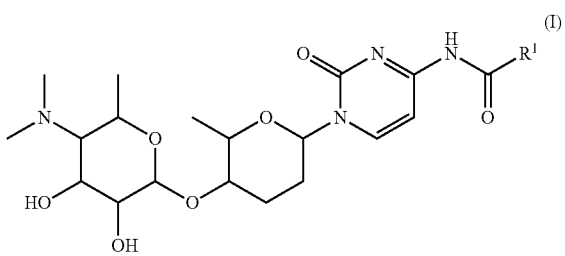

wherein,
R¹ is 2-methylpropan-1-en-yl, 4-(2-methylpropionylamino)-phenyl, 3-methylpentan-1-en-yl, 4-(4-hydroxymethyl-2,2,4-trimethyl-5-oxoimidazolidin-1-yl)-phenyl, 1-methylpropan-1-en-yl, 1-methylpropyl, or 3-methylbutan-l-en-yl
or a salt thereof, or a solvate thereof.

2. The compound according to claim 1, wherein R¹ is 2-methylpropan-1-en-yl.

3. A method for producing the compound or a salt thereof, or a solvate thereof according to claim 1, which comprises:
   a compound accumulation step of culturing in a medium a microorganism which is Streptomyces OPMA40551 strain (Accession No. NITE BP-02510) to accumulate the compound of Formula (I) in the medium; and
   a compound purification step of purifying, from a culture broth of the microorganism, the compound of Formula (I) obtained in the compound accumulation step.

4. A pharmaceutical composition comprising the compound or a pharmaceutically acceptable salt thereof, or a pharmaceutically acceptable solvate thereof according to claim 1, and one or more pharmaceutically acceptable carriers.

5. The pharmaceutical composition according to claim 4 for use in preventing or treating *Mycobacterium avium* complex infection (MAC infection).

TABLE 1

| | MIC (μg/mL) | | | |
|---|---|---|---|---|
| Test compound | *Mycobacterium avium* JCM 15430 strain | *Mycobacterium intracellulare* JCM 6384 strain | *Mycobacterium bovis* BCG Pasteur strain | *Mycobacterium smegmatis* MC²155 strain |
| Compound 40551-F | 0.78 | 0.39 | 1.56 | 3.12 |
| Compound 40551-D | 12.5 | 12.5 | 6.25 | |
| Compound 40551-G | 6.25 | 3.12 | 6.25 | 12.5 |
| Compound 40551-H | 12.5 | 1.56 | 0.39 | 1.56 |
| Compound 40551-I | | 25 | 6.25 | |
| Compound 40551-K | 25 | 6.25 | 6.25 | 25 |
| Compound 40551-L | 3.12 | 0.78 | 1.56 | 3.12 |
| Ethambutol | 12.5 | 3.12 | 1.56 | 0.78 |

6. A method for preventing or treating a symptom, disease and/or disorder which is an infection with one or more bacteria, which comprises administering an effective amount of the compound or a pharmaceutically acceptable salt thereof, or a pharmaceutically acceptable solvate thereof according to according to claim 1 to a subject in need of prevention or treatment of the symptom, disease and/or disorder.

7. The method according to claim 6, wherein the symptom, disease and/or disorder which is an infection with one or more bacteria is one or more symptoms, diseases and/or disorders selected from the group consisting of *Mycobacterium avium* complex infection (MAC infection) and tuberculosis.

* * * * *